United States Patent
Rago et al.

(10) Patent No.: US 11,723,792 B2
(45) Date of Patent: *Aug. 15, 2023

(54) ORAL APPLIANCE DEVICE

(71) Applicant: DIAMOND ORTHOTIC LABORATORY, LLC, La Mesa, CA (US)

(72) Inventors: Matthew M. Rago, San Diego, CA (US); Steven R. Olmos, Alpine, CA (US); Jacob William Smith, Strathfield (AU)

(73) Assignee: DIAMOND ORTHOTIC LABORATORY, LLC, La Mesa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/859,736

(22) Filed: Jul. 7, 2022

(65) Prior Publication Data

US 2022/0401254 A1    Dec. 22, 2022

Related U.S. Application Data

(63) Continuation of application No. 16/359,389, filed on Mar. 20, 2019, now Pat. No. 11,399,975, which is a
(Continued)

(51) Int. Cl.
*A61F 5/56* (2006.01)
*A61F 5/08* (2006.01)

(52) U.S. Cl.
CPC ............... *A61F 5/566* (2013.01); *A61F 5/08* (2013.01)

(58) Field of Classification Search
CPC . A44B 1/30; A47B 37/04; A61F 5/566; A61F 2002/30492; A61F 2005/0158; A61F 5/08; A61C 7/36
See application file for complete search history.

(56) References Cited

U.S. PATENT DOCUMENTS 2,802,269 A    8/1957   Stern
5,277,202 A    1/1994   Hays
(Continued)

FOREIGN PATENT DOCUMENTS

| WO | WO-2011127893 A1 * | 10/2011 | ......... A61C 13/2653 |
| WO | WO2011127893 A1 | 10/2011 | |
| WO | WO2018064772 A1 | 4/2018 | |

OTHER PUBLICATIONS

Espace.net translation of Toussaint WO-2011127893-A1. (Year: 2011).*
(Continued)

*Primary Examiner* — Ophelia A Hawthorne
*Assistant Examiner* — Kevin S Albers
(74) *Attorney, Agent, or Firm* — Roeder & Broder LLP; James P. Broder

(57) ABSTRACT

An oral appliance device (12) for use within a human mouth (10) having an upper jaw (17A) and a lower jaw (17B). The oral appliance device (12) includes an upper appliance member (714), a lower appliance member (712), and a Herbst device assembly (728). The Herbst device assembly (728) movably connects the upper appliance member (714) and the lower appliance member (712) to one another. The Herbst device assembly (728) includes (i) a first Herbst bar (770A), (ii) a second Herbst bar (770B) that adjustably engages the first Herbst bar (770A), (iii) a first Herbst connector assembly (772A) that removably couples the first Herbst bar (770A) to the upper appliance member (714), and (iv) a second Herbst connector assembly (772B) that removably couples the second Herbst bar (770B) to the lower appliance member (712). The Herbst connector assemblies (772A, 772B) are at least partially formed from a nylon-based material. The Herbst bars (770A, 770B) are formed from stainless steel.

20 Claims, 9 Drawing Sheets

Related U.S. Application Data continuation-in-part of application No. 16/355,523, filed on Mar. 15, 2019, which is a continuation-in-part of application No. 15/990,544, filed on May 25, 2018, now abandoned.

(60) Provisional application No. 62/511,902, filed on May 26, 2017.

(56) References Cited

U.S. PATENT DOCUMENTS

| | | | |
|---|---|---|---|
| 5,365,945 A | 11/1994 | Halstrom | |
| 5,727,543 A | 3/1998 | Corsaro | |
| 5,727,805 A | 3/1998 | La Roque | |
| 6,109,265 A | 8/2000 | Frantz | |
| 6,375,667 B1 | 4/2002 | Ruch | |
| 6,467,484 B1 | 10/2002 | De Voss | |
| 6,516,805 B1 | 2/2003 | Thornton | |
| 7,819,122 B2 | 10/2010 | Abramson | |
| 9,999,488 B1 | 6/2018 | Morgan | |
| 10,265,213 B2 | 4/2019 | Shim | |
| 11,399,975 B2 * | 8/2022 | Rago | A61F 5/08 |
| 2004/0177852 A1 | 9/2004 | Abramson | |
| 2005/0241546 A1 | 11/2005 | Royse | |
| 2007/0283967 A1 | 12/2007 | Bailey | |
| 2009/0036889 A1 | 2/2009 | Callender | |
| 2010/0117319 A1 | 5/2010 | Grozev | |
| 2011/0036357 A1 | 2/2011 | Abramson | |
| 2011/0171593 A1 | 7/2011 | Ross | |
| 2011/0232651 A1 | 9/2011 | Diers | |
| 2011/0297162 A1 | 12/2011 | Navarro Segura et al. | |
| 2012/0073582 A1 | 3/2012 | Kopp | |
| 2014/0060549 A1 | 3/2014 | Lucas | |
| 2014/0230829 A1 | 8/2014 | Rogers | |
| 2014/0326253 A1 | 11/2014 | Baratier | |
| 2014/0332011 A1 | 11/2014 | Turek | |
| 2015/0216716 A1 | 8/2015 | Anitua | |
| 2015/0245888 A1 | 9/2015 | Hasegawa | |
| 2015/0272773 A1 | 10/2015 | Rico | |
| 2016/0106572 A1 | 4/2016 | Frantz et al. | |
| 2017/0007371 A1 | 1/2017 | Robichaud | |
| 2017/0035534 A1 | 2/2017 | Ross | |
| 2017/0151086 A1 | 6/2017 | Fareid | |
| 2017/0216084 A1 | 8/2017 | Veis | |
| 2017/0273819 A1 | 9/2017 | Shim et al. | |
| 2017/0304108 A1 | 10/2017 | Simonetti | |
| 2018/0070681 A1 * | 3/2018 | Ryan | A44B 1/32 |
| 2018/0116863 A1 | 5/2018 | Shah | |
| 2018/0153643 A1 | 6/2018 | Lambert | |
| 2018/0186188 A1 | 7/2018 | Lamberg | |
| 2019/0000662 A1 | 1/2019 | Veis | |
| 2019/0125574 A1 * | 5/2019 | Ignacio | A61F 5/566 |
| 2019/0183670 A1 | 6/2019 | Nagai | |
| 2020/0022785 A1 | 1/2020 | Bear | |

OTHER PUBLICATIONS

Oasys Hinge Appliance, Webpage, http://www.dreamsystemsdentallab.com/sleep-devices/oasys-hinge-appliance/.

EMA, Webpage, https://www.myersontooth.com/ema/.

International Search Report and Written Opinion dated May 9, 2019, in PCT Application Serial No. PCT/US2018/034778.

"Herbst Appliance". Link: https://www.saintlukeskc.org/health-library/herbst-appliance. (Year: 2020).

* cited by examiner

ORAL APPLIANCE DEVICE

RELATED APPLICATIONS

The present application is a continuation application claiming the benefit under 35 U.S.C. 120 on co-pending U.S. patent application Ser. No. 16/359,389, filed on Mar. 20, 2019, and entitled "ORAL APPLIANCE DEVICE". Additionally, U.S. patent application Ser. No. 16/359,389 is a continuation-in-part application claiming the benefit under 35 U.S.C. 120 on co-pending U.S. patent application Ser. No. 16/355,523, filed on Mar. 15, 2019, and entitled "ORAL APPLIANCE DEVICE". Additionally, U.S. patent application Ser. No. 16/355,523 is a continuation-in-part application claiming the benefit under 35 U.S.C. 120 on U.S. patent application Ser. No. 15/990,544, filed on May 25, 2018, and entitled "SYSTEMS, METHODS AND ORAL APPLIANCE DEVICES", which claims priority on U.S. Provisional Application Ser. No. 62/511,902, filed on May 26, 2017, and entitled "SYSTEMS, METHODS AND ORAL APPLIANCE DEVICES". As far as permitted, the contents of U.S. patent application Ser. Nos. 16/355,523 and 15/990,544, and U.S. Provisional Application Ser. No. 62/511,902 are incorporated in their entirety herein by reference.

BACKGROUND

Upper airway issues impacting respiration, including upper airway resistance, affect millions of individuals worldwide, and can cause serious medical consequences for the individual. Additionally, such upper airway issues may also cause sleep disruption issues for the individual, such as in the form of snoring, hypopnea and sleep apnea. Hypopnea is a condition characterized by shallow breathing or an abnormally low respiratory rate resulting in reduced air flow. Sleep apnea is a condition characterized by a temporary cessation of breathing that can result in complete cessation of air flow and thus suffocation. These upper airway issues can create conditions requiring the body of the affected individual to expend more effort than usual in order to overcome the reduced airflow. This can result in a fragmentation of sleep patterns due to awakening for short or extended periods of time. As such, these conditions often limit an individual's ability to enter deeper sleep stages that serve the vital function of refreshing and restoring the sleeping individual, and are also damaging to many vital bodily systems and functions.

Additionally, temporomandibular joint and muscle disorders, commonly referred to as "TMJ", are known to cause sleeping problems and can be the cause of craniofacial pain in both children and adults. Various symptoms are associated with craniofacial pain including recurring and chronic headaches; earaches; ear stuffiness or ringing; neck pain or stiffness; facial pain; jaw joint clicking, popping or grating; limited ability to open or close the mouth; jaw locking in either open or closed positions; sensitive, loose or worn down teeth; pain or soreness in the temporomandibular joint; dizziness; pain or difficulty chewing or swallowing; pain behind the eyes; extreme sensitivity to light; attention-deficit hyperactivity disorder (ADHD); bed wetting and others.

Various methods of treatment have been developed as a means to address sleep disruption issues such as snoring, hypopnea and sleep apnea, as well as a means to address issues such as TMJ. For example, one device commonly used for treatment of such issues is referred to as a Continuous Positive Air Pressure (CPAP) device. Such devices deliver pressurized air from a pumping component through a hose and into a mask that is secured over the nose of the individual. Unfortunately, CPAP devices have been unsuccessful for a growing number of patients due to discomfort while using the device, lifestyle issues, and portability problems associated with the device when the individual travels.

Additionally, certain surgical techniques are also available to address such issues for the individual. Unfortunately, such surgical techniques suffer drawbacks such as high costs, lack of reversibility, risk of harm, e.g., permanent physical damage, to the individual, and extensive and often painful recovery periods.

Further, various types of non-invasive devices have also been developed in an attempt to alleviate or eliminate such issues for the individual. Some such devices focus on improving airflow through the nose, with some devices being attached to the external skin on either side of the nose, and other devices being designed to fit within the nasal passageway and push the inner walls of the nose outward to expand the air passageways. Unfortunately, such devices can irritate the skin and/or can irritate the sensitive inner lining of the nasal passageway, thereby making such devices uncomfortable and awkward to use.

Other such devices focus on repositioning the lower jaw or mandible in an anterior or forward position. This orientation can pull the base of the tongue forward within the mouth and thereby increase the size of the air passage in the posterior pharyngeal region, which is the breathing passage behind the base of the tongue. Some such devices are non-adjustable devices, and thus may not be appropriate if there is a change in the position of the lower jaw relative to the upper jaw. Other such devices are adjustable devices, but they typically take up more space within the mouth and restrict tongue space which can inhibit the tongue from moving forward as desired. Such devices may also adversely impact the ability of the individual to close their lips, which can make the device uncomfortable to wear and inhibit the individual's ability to change positions during sleep.

Due to the varied nature of symptoms and potential negative results caused by snoring, hypopnea, sleep apnea, and TMJ, it is desirable to treat these conditions using a non-invasive apparatus that does not suffer the drawbacks and disadvantages of current devices.

SUMMARY

The present invention is directed toward an oral appliance device for use within a human mouth having an upper jaw and a lower jaw. In various embodiments, the oral appliance device includes an upper appliance member, a lower appliance member, and a Herbst device assembly. The upper appliance member selectively engages upper teeth within the human mouth. The lower appliance member selectively engages lower teeth within the human mouth. The Herbst device assembly movably connects the upper appliance member and the lower appliance member to one another, the Herbst device assembly including (i) a first Herbst bar, (ii) a second Herbst bar that adjustably engages the first Herbst bar, (iii) a first Herbst connector assembly that removably couples the first Herbst bar to the upper appliance member, and (iv) a second Herbst connector assembly that removably couples the second Herbst bar to the lower appliance member, the Herbst connector assemblies being at least partially formed from a nylon-based material, the Herbst bars being formed from stainless steel.

In certain embodiments, the first Herbst bar and the second Herbst bar adjustably engage one another to selectively control positioning of the lower jaw relative to the upper jaw.

In various embodiments, the first Herbst bar and the second Herbst bar adjustably engage one another in a telescoping manner.

In some embodiments, each of the Herbst connector assemblies includes a coupling base that is integrally formed with one of the appliance members, the coupling base including a first base aperture.

In certain embodiments, each of the Herbst connector assemblies includes a coupling insert including a first insert aperture having internal threads.

In some embodiments, each of the Herbst connector assemblies includes a coupling button including a button shaft that is removably received and retained within the first insert aperture.

In various embodiments, the Herbst connector assemblies are manufactured using one of a three-dimensional printer and a selective laser sintering process.

In certain embodiments, the upper appliance member is formed from a nylon-based material.

In some embodiments, the lower appliance member is formed from a nylon-based material.

In various embodiments, each of the Herbst connector assemblies includes (i) a coupling base that is integrally formed with one of the appliance members, the coupling base including a first base aperture; (ii) a coupling insert that is selectively positioned substantially within the first base aperture, the coupling insert including a first insert aperture; and (iii) a coupling button including a button shaft that is removably received and retained within the first insert aperture.

In certain embodiments, the first insert aperture has internal threads; and wherein the button shaft includes external threads that are configured to threadingly engage the internal threads of the first insert aperture.

In some embodiments, each of the Herbst bars includes a bar end having a bar aperture; and wherein the button shaft is configured to extend through the bar aperture and be threaded into the first insert aperture to removably couple the first Herbst bar to the upper appliance member and to removably couple the second Herbst bar to the lower appliance member.

The present invention is also directed toward an oral appliance device for use within a human mouth having an upper jaw and a lower jaw. In various embodiments, the oral appliance device includes an upper appliance member, a lower appliance member, and a Herbst device assembly. The upper appliance member selectively engages upper teeth within the human mouth. The lower appliance member selectively engages lower teeth within the human mouth. The Herbst device assembly including (i) a first Herbst bar, (ii) a second Herbst bar that adjustably engages the first Herbst bar to selectively control positioning of the lower jaw relative to the upper jaw, (iii) a first Herbst connector assembly that removably couples the first Herbst bar to the upper appliance member, and (iv) a second Herbst connector assembly that removably couples the second Herbst bar to the lower appliance member, the Herbst connector assemblies being at least partially formed from a nylon-based material, the Herbst bars being formed from stainless steel. Each of the Herbst connector assemblies includes (i) a coupling base that is integrally formed with one of the appliance members, the coupling base including a first base aperture; (ii) a coupling insert that is selectively positioned substantially within the first base aperture, the coupling insert including a first insert aperture having internal threads; and (iii) a coupling button including a button shaft having external threads that are configured to threadingly engage the internal threads of the first insert aperture so that the button shaft is removably received and retained within the first insert aperture.

In certain embodiments, the first Herbst bar and the second Herbst bar adjustably engage one another in a telescoping manner.

In some embodiments, each of the Herbst bars includes a bar end having a bar aperture; and wherein the button shaft is configured to extend through the bar aperture and be threaded into the first insert aperture to removably couple the first Herbst bar to the upper appliance member and the second Herbst bar to the lower appliance member.

In various embodiments, the coupling base has a pair of second base apertures; wherein the coupling insert has a pair of second insert apertures; and wherein each Herbst connector assembly further includes a coupling pin that is positioned to extend through both of the second base apertures and both of the second insert apertures so that the coupling insert is retained within the coupling base.

In certain embodiments, the coupling base, the coupling insert, and the coupling button are each formed from a nylon-based material In some embodiments, the coupling base, the coupling insert, and the coupling button are each manufactured using one of a three-dimensional printer and a selective laser sintering process.

In various embodiments, the upper appliance member and the lower appliance member are formed from a nylon-based material.

The present invention is further directed toward an oral appliance device for use within a human mouth having an upper jaw and a lower jaw. In various embodiments, the oral appliance device includes an upper appliance member, a lower appliance member, and a Herbst device assembly. The upper appliance member selectively engages upper teeth within the human mouth. The lower appliance member selectively engages lower teeth within the human mouth. The Herbst device assembly assembly including (i) a first Herbst bar, (ii) a second Herbst bar that adjustably engages the first Herbst bar to selectively control positioning of the lower jaw relative to the upper jaw, (iii) a first Herbst connector assembly that removably couples the first Herbst bar to the upper appliance member, and (iv) a second Herbst connector assembly that removably couples the second Herbst bar to the lower appliance member. Each of the Herbst connector assemblies including (i) a coupling base that is integrally formed with one of the appliance members, the coupling base including a first base aperture and a pair of second base apertures; (ii) a coupling insert that is selectively positioned in the first base aperture, the coupling insert including a first insert aperture and a pair of second insert apertures; (iii) a coupling button including a button shaft that is removably received and retained within the first insert aperture, and (iv) a coupling pin that is positioned to extend through both of the second base apertures and both of the second insert apertures so that the coupling insert is retained in the coupling base.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Embodiments of the present invention are described herein in the context of an oral appliance device. In particular, as described in detail herein, various embodiments of the oral appliance device are uniquely designed and/or are uniquely formed to overcome and/or inhibit upper airway issues from causing sleep disruption issues for an individual, such as in the form of snoring, hypopnea and sleep apnea. For example, as provided herein, the oral appliance device can incorporate a modular design with removable and/or exchangeable components, which uses unique materials and/or manufacturing processes that can provide various benefits and advantages for the patients using the oral appliance device as well as the healthcare professionals providing such devices, in comparison to traditional oral appliance devices. Additionally, in some embodiments, the oral appliance device can provide a nasal and lingual breathing aid that acts intraorally and can be fixed in place by selective attachment to the oral appliance device (or removed) depending on patient compatibility. Further, embodiments of the oral appliance device are further usable to overcome and/or inhibit temporomandibular joint and muscle disorders, i.e. TMJ, which can also cause sleeping problems and/or be the cause of craniofacial pain in the individual.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same or similar nomenclature and/or reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
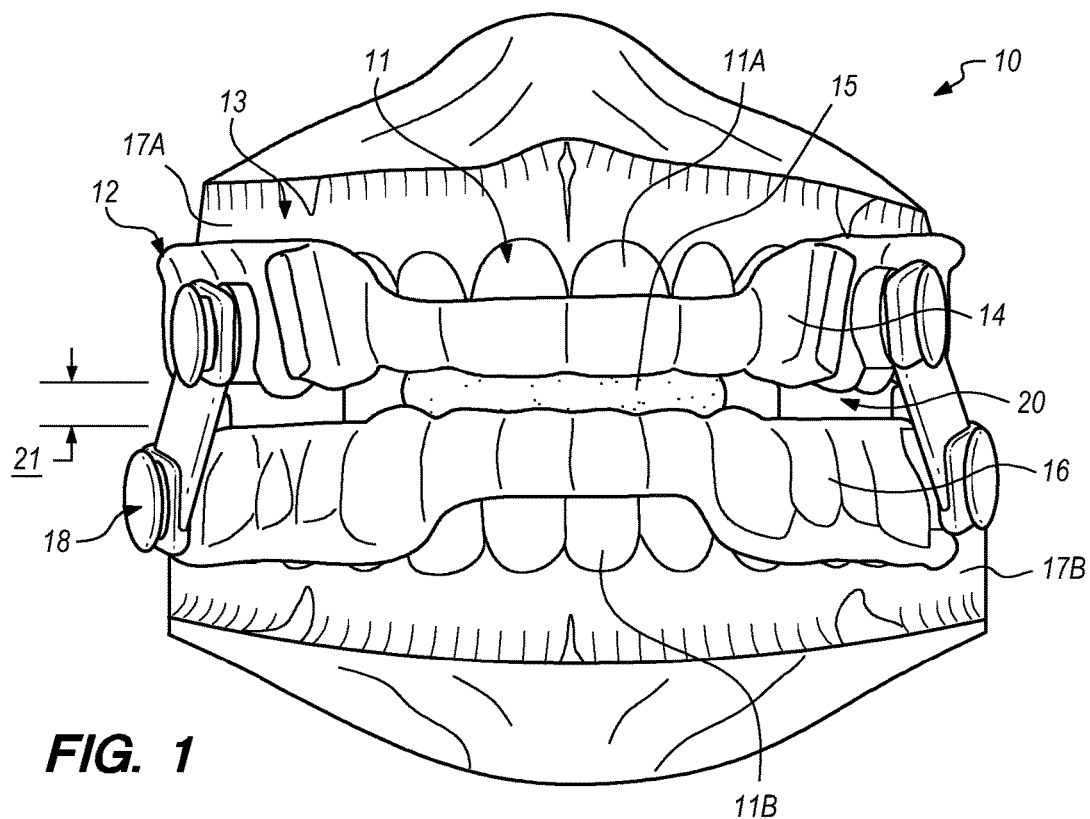
FIG. 1 is a simplified front view illustration of a human mouth and an embodiment of an oral appliance device having features of the present invention that is positioned within the mouth.

FIG. 1 is a simplified front view illustration of a human mouth 10 (also referred to herein simply as a "mouth") including a plurality of teeth 11, and an embodiment of an oral appliance device 12 having features of the present invention that is positioned within the mouth 10. More particularly, as shown, the oral appliance device 12 is positioned to selectively engage the plurality of teeth 11 within the mouth 10.

As noted, the mouth 10 can include a plurality of teeth 11, i.e. a plurality of upper teeth 11A and a plurality of lower teeth 11B. Also shown in FIG. 1, the mouth 10 can further include interior features such as the buccal sulcus 13. There are four buccal sulcus 13 in the mouth 10 and each is known generally as a depression having a width extending between a cheek and an alveolar process of the arch, where the arch is known as the composite structure of the teeth. Each buccal sulcus 13 begins at a buccal frenum toward the front of the mouth 10 and extends to the back of the mouth 10. As such, each buccal sulcus 13 is oriented generally front to back in the mouth 10 above and outside the teeth 11 and inside the gums.

It is appreciated that when determining the most effective patient treatment, a healthcare professional may need to capture oral or other impressions of the patient's face and head. For example, an accurate impression of the buccal sulcus 13 can be essential for the correct positioning of nasal dilators (i.e. for dilating a nasal passage (not shown)), tongue positioners (i.e. for affecting the positioning of a tongue 15 within the mouth 10), jaw positioners (i.e. for controlling a relative position between an upper jaw 17A and a lower jaw 17B within the mouth 10) and/or other components which may be required in patient treatment in order to open the patient's airway. Unfortunately, this area can be difficult to capture with impressions, especially digital impressions due to its location and discomfort to the patient. However, without an accurate impression, a dental laboratory would find it extremely difficult or impossible to fabricate a therapeutic oral appliance device with proper function. Current oral appliance systems used for capturing digital impressions are generally unitary, and therefore not adjustable. As such, if a doctor or dentist wishes to adjust the oral appliance device to a different position, the entire oral appliance device must be sent to the dental laboratory to have the incorrect modification removed and a replacement fabricated. The patient is rarely present at the laboratory when the adjustments are being made to the replacement device. As such, the laboratory will estimate or guess what position the nasal dilator and/or other components should be placed to provide the most effective and comfortable treatment. If the laboratory is incorrect in their assessment, the process of sending it from the dental practice back to the dental laboratory will repeat leading to patient and staff frustration.

Thus, a modular system that allows a doctor, dentist or other healthcare professional to freely remove, change or adjust such components associated with the oral appliance device 12 into a functional position, as described in detail herein, without sending the entire system to a laboratory for re-fabrication would provide the best patient care outcome without cause for lapse in conditions. Accordingly, various embodiments of the oral appliance device 12, as described herein, include a modular design that can more effectively and efficiently result in reduced costs, saved time, improved comfort, convenience and functionality, and a more effective overall patient treatment. Further, various embodiments disclosed herein provide oral appliance devices 12 which are less bulky, more durable, and which are contained solely within the oral cavity.

The design of the oral appliance device 12 can be varied to suit the particular patient as well as the particular issues to be addressed. In various embodiments, as shown in FIG. 1, the oral appliance device 12 can include an upper appliance member 14 that is configured to selectively engage and/or be secured or coupled to the upper teeth 11A, and a lower appliance member 16 that is configured to selectively engage and/or be secured or coupled to the lower teeth 11B. Additionally, in some embodiments, the oral appliance device 12 can further include a connector assembly 18 for selectively and movably connecting the upper appliance member 14 and the lower appliance member 16 to one another. Further, as illustrated, the oral appliance device 12 can also include a teeth spacing assembly 20 that is configured to selectively adjust and/or maintain a teeth spacing 21 between the upper teeth 11A and the lower teeth 11B within the mouth 10. As utilized herein, the "teeth spacing" between the upper teeth 11A and the lower teeth 11B that is adjusted and/or maintained through the use of the teeth spacing assembly 20 is the spacing between the upper teeth 11A and the lower teeth 11B that is caused solely by components of the oral appliance device 12 and not by relative movement between the teeth 11A, 11B and appliance members 14, 16 created by voluntary movements of the mouth 10 and teeth 11 of the patient.

It is appreciated that the oral appliance device 12 can include more components or fewer components than those specifically shown in FIG. 1. For example, as described in greater detail herein below, in certain embodiments, the oral appliance device 12 can also include one or more of (i) a nasal dilator assembly 422 (illustrated in FIG. 4A) that opens up the nasal passageway while not irritating or acting as an obtrusive object in the buccal sulcus 13, (ii) a tongue positioner assembly 524 (illustrated in FIG. 5A) that helps to maintain maximum intraoral tongue space in comparison to previous oral appliance devices, (iii) a jaw position controller 626 (illustrated in FIG. 6A, and also sometimes referred to herein as a "jaw positioner") that can function as a mandibular stop, thus inhibiting the lower jaw 17B from falling back in a supine position, and therefore inhibiting collapse of the airway, and (iv) a Herbst device assembly 728 (illustrated in FIG. 7A) that can also control the positioning of the lower jaw 17B so as to inhibit the lower jaw 17B from falling back and potentially blocking the upper airway of the individual. It is also appreciated that the connector assembly 18, the teeth spacing assembly 20, the nasal dilator assembly 422, the tongue positioner assembly 524, the jaw position controller 626, and the Herbst device assembly 728 can be used individually or in any suitable combination within any given embodiment of the oral appliance device 12. Additionally, or in the alternative, it is further appreciated that individual embodiments of the oral appliance device 12 need not include the connector assembly 18 and/or the teeth spacing assembly 20.

As an overview, the oral appliance device 12 of the present invention is uniquely configured in various alternative embodiments to provide improved airflow through nasal and pharyngeal air passages, thus overcoming and/or inhibiting issues within the upper airway of an individual from causing sleep disruption issues for the individual, e.g., in the form of snoring, hypopnea and/or sleep apnea. It is further appreciated that such embodiments of the oral appliance device 12 can also function to overcome and/or inhibit any potential issues with temporomandibular joint and muscle disorders.

Additionally, as provided herein, the various components of the oral appliance device 12 can be formed from materials and/or formed from a unique process that can save time and money, as well as improving overall patient treatment options. For example, as described herein, various embodiments of the oral appliance device 12 and/or the specific components included therewith can be formed from nylon-based materials such as PA2200 nylon, polyamide 12 nylon, or other suitable nylon-based materials. Further, in many applications, the oral appliance device 12 and/or the specific components included therewith can be created or manufactured using a three-dimensional (3-D) printer or a selective laser sintering (SLS) process. With such processes, any components of the oral appliance device 12 can be quickly and easily made or remade without the need for additional models or impressions being formed, which can otherwise greatly slow down the overall treatment process. Additionally, in various embodiments, flexible printed material can allow less bulky fabrication of oral appliance devices 12 than previously developed devices that are equal if not more durable than such previous oral appliance devices. Since these materials are less bulky, they are better able to maintain the tongue 15 in a forward position while reducing airflow resistance through the pharyngeal region, thus preventing the tongue 15 from falling backward in a supine position. This can be beneficial since the position of the tongue 15 plays a large role in airway obstruction at rear positioned tongue regions.

Those in the art will recognize that patients who may misplace their individualized oral appliance device are able to have a new one fabricated quickly by a laboratory when using printed designs. This provides the benefit of reduced or eliminated requirements for medical professionals to create new records, saving time and money by improving efficiency. This also provides the benefit of allowing for manufacturing of replacement oral appliance devices and/or the individual components thereof that are substantially identical to the originals without requiring additional appointments to be scheduled or records to be created. Thus, patients are provided optimal comfort with minimal time requirements. Another benefit is the added advantage of time savings for healthcare professionals in the form of a reduction in time required to adjust these oral appliance devices and their associated components, such as teeth spacers, nasal dilators, tongue positioners, jaw positioners, etc., when modifying or correcting positioning.

Based on the advantages of the modular designs disclosed herein, any damaged or destroyed components for the oral appliance device 12 can be quickly and easily replaced in the office by the healthcare professional. This removes the need to send the oral appliance device 12 back to a laboratory for adjustments. Thus, patients do not have to suffer unnecessarily without their oral appliance devices. For example, if the patient is non-compliant, both the nasal dilators and tongue positioners can be removed without lessening the integrity of the oral appliance device 12 and without causing discomfort to the patient.

Figure 2A:
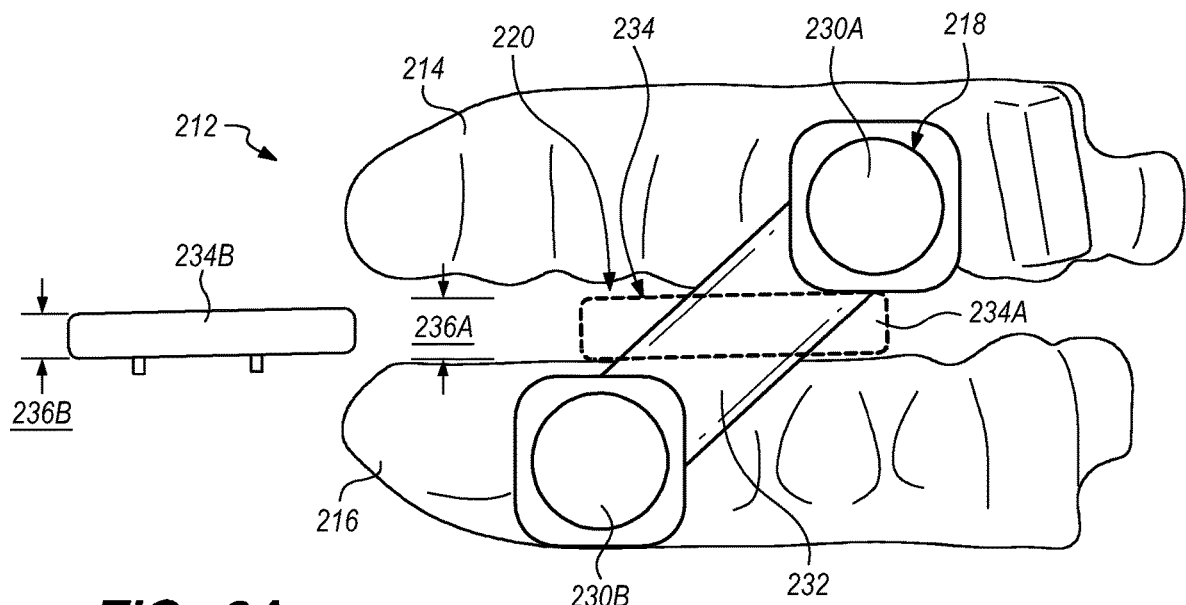
FIG. 2A is a simplified side view illustration of an embodiment of the oral appliance device.

FIG. 2A is a simplified side view illustration of an embodiment of the oral appliance device 212. As shown in this embodiment, the oral appliance device 212 includes the upper appliance member 214, the lower appliance member 216, the connector assembly 218 and the teeth spacing assembly 220. In certain non-exclusive alternative embodiments, the oral appliance device 212 can further include one or more of the nasal dilator assembly 422 (illustrated in FIG. 4A), the tongue positioner assembly 524 (illustrated in FIG. 5A) and the jaw position controller 626 (illustrated in FIG. 6A).

As provided above, during use of the oral appliance device 210, the upper appliance member 214 is positioned to selectively engage the upper teeth 11A (illustrated in FIG. 1) and the lower appliance member 216 is positioned to selectively engage the lower teeth 11B (illustrated in FIG. 1).

In various embodiments, the upper appliance member 214 and/or the lower appliance member 216 may provide a frame which other components, e.g., components of the connector assembly 218 and/or components of the teeth spacing assembly 220, can be permanently or removably secured with or mounted to. More specifically, the upper appliance member 214 is generally a casting mouthpiece of a patient's maximal, superior or upper dental arch. Additionally, the upper appliance member 214 can include a custom-molded mouthpiece that includes at least one flat occlusal, upper member surface 214A (illustrated in FIG. 2B) that can be approximately located below a portion of all of the area between a second bicuspid and a first molar along both extensions, arms, or sides of the upper appliance member 214 and positioned facing downward toward the inferior, mandibular or lower dental arch. As such, the flat occlusal, upper member surface 214A can function as a posterior vestibular support pad, and which can provide the patient with occlusion that is free from occlusal or other forces during operation.

Somewhat similarly, the lower appliance member 216 is generally a casting mouthpiece of a patient's mandibular, inferior or lower dental arch. Additionally, the lower appliance member can be a custom-molded mouthpiece that includes at least one flat occlusal, lower member surface 216A (illustrated in FIG. 2C) along both extensions, arms or sides of the lower appliance member 216 and facing upward toward the superior, maximal or upper dental arch.

In certain embodiments, the upper appliance member 214 and the lower appliance member 216 can be formed from any suitable materials and/or can be formed from any suitable manufacturing process. For example, in some non-exclusive embodiments, the upper appliance member 214 and/or the lower appliance member 216 can be formed from a nylon-based material, e.g., PA 2200 nylon, polyamide 12 nylon, or another suitable nylon material. Alternatively, the upper appliance member 214 and/or the lower appliance member 216 can be formed from other suitable materials. For example, in certain non-exclusive alternative embodiments, the upper appliance member 214 and/or the lower appliance member 216 can use appropriate and effective materials such as using a processed acrylic that has a hard-molded outer shell and, optionally may include a soft inner lining, to capture the patient's maximal dental arch and the patient's mandibular dental arch, respectively. Manufacturing processes for such alternative materials can include the use of "boil-and-bite" materials, pre-formed or pre-fabricated common arch forms, or other processes and materials currently known in the art. In still other embodiments, the upper appliance member 214 and/or the lower appliance member 216 can be formed from a thermoplastic material, which can be heat molded over a dental model of the patient's teeth.

Additionally, in certain non-exclusive alternative embodiments, the upper appliance member 214 and/or the lower appliance member 216 can be manufactured using one of a three-dimensional printer and a selective laser sintering process. With such design, the upper appliance member 214 and the lower appliance member 216 can be quickly and easily made or remade from a single model without the need for additional impressions or models. Alternatively, the upper appliance member 214 and/or the lower appliance member 216 can be manufactured using another suitable process.

As noted above, the connector assembly 218 is provided such that the upper appliance member 214 and the lower appliance member 216 can be selectively and movably connected to one another. This results in the upper appliance member 214 and the lower appliance member 216 being able to be effectively utilized in conjunction with one another, and while still allowing the patient to move their upper teeth 11A (and upper jaw 17A (illustrated in FIG. 1)), and their lower teeth 11B (and lower jaw 17B (illustrated in FIG. 1)), relative to one another. Additionally, the connector assembly 218 is further configured to inhibit the lower jaw 17B from falling back in a supine position and potentially blocking the upper airway of the individual. In some embodiments, the connector assembly 218 is configured to enable the upper appliance member 214 and the lower appliance member 216 to move relative to one another and/or to allow for protrusive titration between the appliance members 214, 216 of between approximately one millimeter and five millimeters. Alternatively, the connector assembly 218 can be configured to enable the upper appliance member 214 and the lower appliance member 216 to move relative to one another and/or to allow for protrusive titration between the appliance members 214, 216 of less than approximately one millimeter or greater than approximately five millimeters.

The connector assembly 218 can have any suitable design for purposes of having the upper appliance member 214 and the lower appliance member 216 be selectively and movably connected to one another. For example, as shown in FIG. 2A, the connector assembly 218 can include a first connector button 230A that is removably secured to the upper appliance member 214, a second connector button 230B that is removably secured to the lower appliance member 216, and a connector band 232 that is selectively secured or coupled to each of the upper appliance member 214 and the lower appliance member 216, e.g., via the first connector button 230A and the second connector button 230B, respectively. Alternatively, the connector assembly 218 can have another suitable design. The connector assembly 218 will be described in greater detail herein below in relation to FIGS. 3A and 3B.

The teeth spacing assembly 220 is configured to enable the adjustment and maintaining of a desired teeth spacing 21

(illustrated in FIG. 1) between the upper teeth 11A and the lower teeth 11B. Stated in another manner, the teeth spacing assembly 220 is configured such that the upper appliance member 214 and the lower appliance member 216, and thus the upper teeth 11A and the lower teeth 11B, cannot be positioned directly adjacent to one another within the mouth 10 (illustrated in FIG. 1) of the patient.

The design of the teeth spacing assembly 220 can be varied. In various embodiments, the teeth spacing assembly 220 includes a plurality of vertical shims 234 that can be alternatively, removably secured to one of the upper appliance member 214 and the lower appliance member 216, e.g., with features that can be encompassed and/or integrally formed within the vertical shim 234 and the appliance member 214, 216 to which the vertical shim 234 is being secured or coupled. As shown in FIG. 2A, when the vertical shim 234 is secured or coupled to one of the appliance members 214, 216, the vertical shim 234 is positioned substantially directly between the upper appliance member 214 and the lower appliance member 216 so as to define the teeth spacing 21 between the upper teeth 11A and the lower teeth 11B.

It is appreciated that each of the plurality of vertical shims 234 can have a different shim height such that the teeth spacing 21 between the upper teeth 11A and the lower teeth 11B can be adjusted as desired. More particularly, in certain embodiments, the teeth spacing assembly 220 can include at least a first vertical shim 234A having a first shim height 236A, and a second vertical shim 234B having a second shim height 236B that is different than the first shim height 236B. In such embodiments, (i) the first vertical shim 234A can be utilized such that the upper teeth 11A are spaced apart from the lower teeth 11B by a teeth spacing 21 of at least the first shim height 236A when the first vertical shim 234A is secured or coupled to one of the appliance members 214, 216; and (ii) the second vertical shim 234B can be utilized such that the upper teeth 11A are spaced apart from the lower teeth 11B by a teeth spacing 21 of at least the second shim height 236B when the second vertical shim 234B is secured or coupled to one of the appliance members 214, 216. It is further appreciated that each of the vertical shims 234 can be used alternatively to each of the other vertical shims 234, and/or multiple vertical shims 234 can be used in conjunction with one another to provide even further options for the teeth spacing 21 between the upper teeth 11A and the lower teeth 11B. For example, in one non-exclusive alternative application, the first vertical shim 234A can be selectively secured or coupled to the upper appliance member 214 and the second vertical shim 234B can be selectively secured or coupled to the lower appliance member 216 such that the upper teeth 11A are spaced apart from the lower teeth 11B by a teeth spacing 21 of at least the first shim height 236A plus the second shim height 236B.

In certain non-exclusive embodiments, the teeth spacing 21 that is created by using any individual vertical shim 234 and/or any combination of vertical shims 234 can vary between approximately one millimeter and five millimeters. Alternatively, in other embodiments, the vertical shims 234 can be sized and used individually or in combination with other vertical shims 234 to create teeth spacing 21 that is less than approximately one millimeter or greater than approximately five millimeters.

Additionally, during use of the oral appliance device 212 within the mouth 10 of the patient including the use of the teeth spacing assembly 220, the upper appliance member 214 and the lower appliance member 216 are movable relative to one another between an open configuration and a closed configuration. As utilized herein, the "closed configuration" is defined as when at least one of the vertical shims 234 is positioned between the appliance members 214, 216, and there is no air space between the vertical shims 234 and either of the appliance member 214, 216, and/or between vertical shims 234 that are used in combination with other vertical shims 234 in a stacked relationship. Stated in another manner, when in the closed configuration, the upper appliance member 214 (and thus the upper teeth 11A) and the lower appliance member 216 (and thus the lower teeth 11B) are as close as possible to one another except for the presence of the vertical shim(s) 234 that are positioned between the appliance members 214, 216. Conversely, the "open configuration" is defined as when at least one of the vertical shims 234 is positioned between the appliance members 214, 216, and there is air space between the vertical shims 234 and one of the appliance members 214, 216 (i.e. the appliance member 214, 216 which the vertical shim 234 is not removably secured to), and/or between vertical shims 234 that are used in combination with other vertical shims 234 in a stacked relationship.

In various embodiments, each of the vertical shims 234 can be formed from any suitable materials and/or can be formed from any suitable manufacturing process. For example, in some non-exclusive embodiments, each of the vertical shims 234 can be formed from a nylon-based material, e.g., PA 2200 nylon, polyamide 12 nylon, or another suitable nylon material. Alternatively, each of the vertical shims 234 can be formed from other suitable materials.

Additionally, in certain non-exclusive alternative embodiments, each of the vertical shims 234 can be manufactured using one of a three-dimensional printer and a selective laser sintering process. With such design, each of the vertical shims 234 can be quickly and easily made or remade from a single model without the need for additional impressions or models. Alternatively, each of the vertical shims 234 can be manufactured using another suitable process.

Figure 2B:
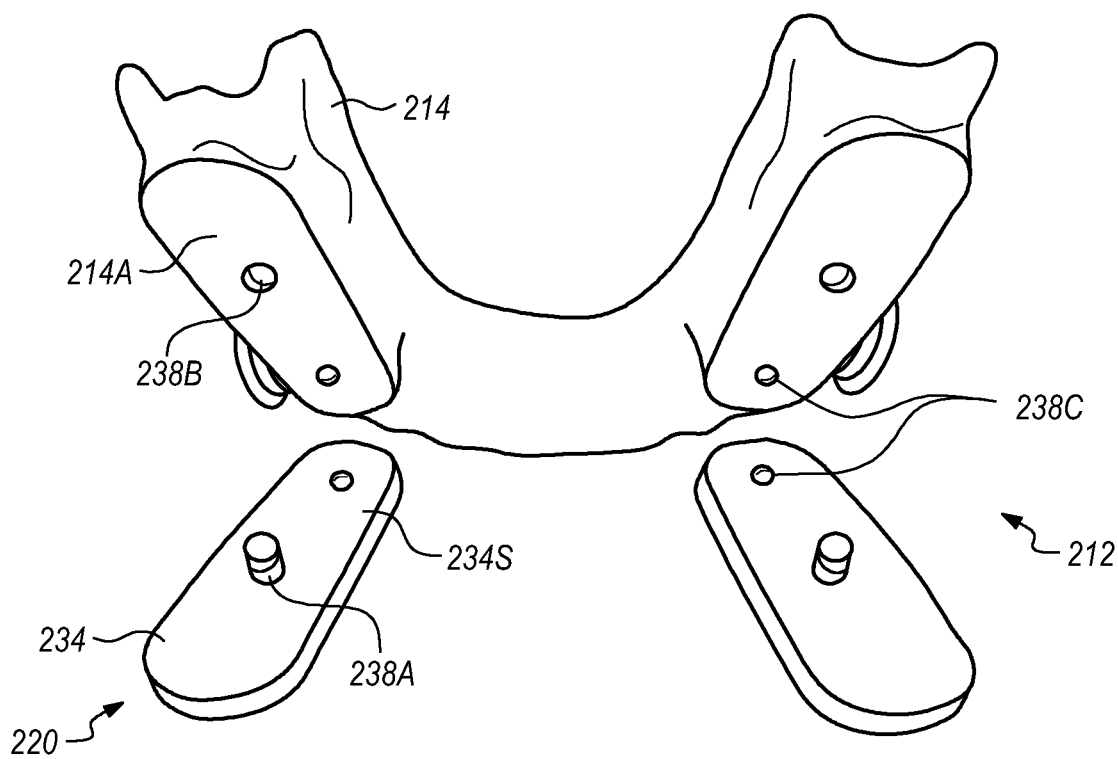
FIG. 2B is a partially exploded view illustration of a portion of the oral appliance device illustrated in FIG. 2A.

FIG. 2B is a partially exploded view illustration of a portion of the oral appliance device 212 illustrated in FIG. 2A. More particularly, FIG. 2B is an illustration of the upper appliance member 214 and at least a portion of the teeth spacing assembly 220. As shown in FIG. 2B, the teeth spacing assembly 220 includes a pair of vertical shims 234, with one vertical shim 234 being configured to be removably secured to each side of the upper appliance member 214.

The vertical shims 234 and/or the upper appliance member 214 can include any suitable design features in order to selectively and/or removably couple the vertical shims 234 to the upper appliance member 214. In certain embodiments, as shown, the vertical shim 234 can include an appliance engager 238A that is integrally formed as part of the vertical shim 234, and the upper appliance member 214 can include a shim receiver 238B that is integrally formed as part of the upper appliance member 214. In such embodiments, the appliance engager 238A is configured to selectively engage the shim receiver 238B so that the vertical shim 234 can be removably secured to the upper appliance member 214. In one such embodiment, the appliance engager 238A can be provided in the form of a coarsely threaded post or screw that extends away from a shim surface 234S, which is configured to rotatably engage the shim receiver 238B, e.g., a coarsely threaded aperture, that is formed into the upper member surface 214A of the upper appliance member 214. With such design, the appliance engager 238A can be rotatably and/or threadingly received within the shim receiver 238B. Additionally, in such embodiment, the vertical shim 234 is movable between a disengaged configuration, wherein when in the disengaged configuration the vertical shim 234 can be selectively secured or coupled to and removed from the upper appliance member 214, and an engaged configuration, wherein when in the engaged configuration the vertical shim 234 cannot be removed from the upper appliance member 214.

Further, in some embodiments, the vertical shim 234 and/or the upper appliance member 214 can also include an alignment system 238C, e.g., a small bump and recess combination, to more effectively align the coupling between the vertical shim 234 and the upper appliance member 214 when the vertical shim 234 is in the engaged configuration. More particularly, in such embodiments, when properly aligned with the vertical shim 234 in the engaged configuration, the small bump on one of the vertical shim 234 and the upper appliance member 214 will fit and be retained within the small recess on the other of the vertical shim 234 and the upper appliance member 214. Alternatively, the vertical shim 234 and/or the upper appliance member 214 can be designed without the alignment system 238C.

It is appreciated that a similar design can be incorporated into a removable coupling between the vertical shims 234 and the lower appliance member 216 (illustrated in FIG. 2A).

Additionally, or in the alternative, the appliance engager 238A of the vertical shim 234 and/or the shim receiver 238B of the upper appliance member 214 can have another suitable design. For example, in one non-exclusive alternative embodiment, the appliance engager 238A can be provided in the form of at least one post that extends away from a shim surface 234S of the vertical shim 234, and the shim receiver 238B can be provided in the form of at least one aperture that is formed into the surface 214A of the upper appliance member 214. With such design, each of the at least one aperture of the shim receiver 238B is sized and shaped to receive one of the at least one post of the appliance engager 238A, such that the vertical shim 234 can be removably secured to the upper appliance member 214.

As shown, when the vertical shim 234 is removably secured to the upper appliance member 214, the shim surface 234S of the vertical shim 234 is positioned substantially directly adjacent to the upper member surface 214A of the upper appliance member 214.

Figure 2C:
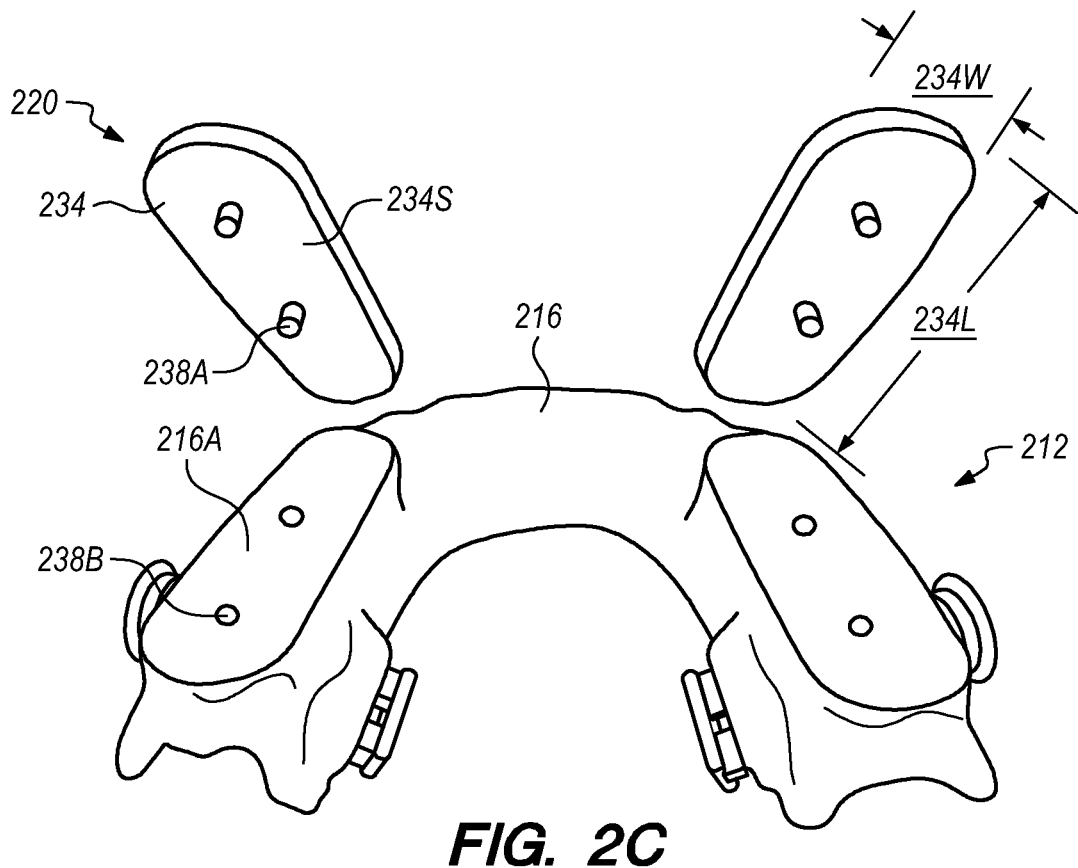
FIG. 2C is a partially exploded view illustration of another portion of the oral appliance device illustrated in FIG. 2A.

FIG. 2C is a partially exploded view illustration of another portion of the oral appliance device 212 illustrated in FIG. 2A. More particularly, FIG. 2C is an illustration of the lower appliance member 216 and at least a portion of the teeth spacing assembly 220. As shown in FIG. 2C, the teeth spacing assembly 220 includes a pair of vertical shims 234, with one vertical shim 234 being configured to be removably secured to each side of the lower appliance member 216.

The vertical shim 234 and/or the lower appliance member 216 can include any suitable design features in order to selectively and/or removably couple the vertical shims 234 to the lower appliance member 216. In certain embodiments, as shown, the vertical shim 234 can include an appliance engager 238A that is integrally formed as part of the vertical shim 234, and the lower appliance member 216 can include a shim receiver 238B that is integrally formed as part of the lower appliance member 216. In such embodiments, the appliance engager 238A is configured to selectively engage the shim receiver 238B so that the vertical shim 234 can be removably secured to the lower appliance member 216. In one such embodiment, the appliance engager 238A can be provided in the form of at least one post (two are shown on each vertical shim 234 in FIG. 2C) that extends away from a shim surface 234S of the vertical shim 234, and which are configured to engage the shim receiver 238B, e.g., at least one aperture (two are shown on each side of the lower appliance member 216), that is formed into the lower member surface 216A of the lower appliance member 216. With such design, each of the at least one aperture of the shim receiver 238B is sized and shaped to receive one of the at least one post of the appliance engager 238A, such that the vertical shim 234 can be selectively and removably secured to the lower appliance member 216.

It is appreciated that a similar design can be incorporated into a removable coupling between the vertical shims 234 and the upper appliance member 214 (illustrated in FIG. 2A).

Additionally, or in the alternative, the appliance engager 238A of the vertical shim 234 and/or the shim receiver 238B of the lower appliance member 216 can have another suitable design. For example, in one non-exclusive alternative embodiment, the appliance engager 238A can be provided in the form of a coarsely threaded post or screw that extends away from the shim surface 234A, which is configured to rotatably engage the shim receiver 238B, e.g., a coarsely threaded aperture, that is formed into the lower member surface 216A of the lower appliance member 216. With such alternative design, the vertical shim 234 can be movable between a disengaged configuration, wherein when in the disengaged configuration the vertical shim 234 can be selectively secured or coupled to and removed from the lower appliance member 216, and an engaged configuration, wherein when in the engaged configuration the vertical shim 234 cannot be removed from the lower appliance member 216.

As shown, when the vertical shim 234 is removably secured to the lower appliance member 216, the shim surface 234S of the vertical shim 234 will be positioned substantially directly adjacent to the lower member surface 216A of the lower appliance member 216.

As noted above, the teeth spacing assembly 220 can alternatively use any of a plurality of vertical shims 234 of different shim heights 236A, 236B (illustrated in FIG. 2A) by removably coupling the vertical shim(s) 234 to one of the appliance members 214, 216. Additionally, as shown in FIG. 2C, each of the vertical shims 234 can be said to have a shim length 234L and a shim width 234W, in addition to the shim height 236A, 236B. It is appreciated that in addition to the alternative use of vertical shims 234 having different shim heights 236A, 236B, the teeth spacing assembly 220 can also include alternative vertical shims 234 having different shim lengths 234L and/or different shim widths 234W. The use of any such alternative vertical shims 234 as part of the teeth spacing assembly 220, i.e. having different shim lengths 234L, shim widths 234W and/or shim heights 236A, 236B, is to provide the healthcare professional and/or the patient with suitable options to better fit the particular size and shape of the mouth 10 (illustrated in FIG. 1) of the patient, as well as being better able to provide the desired treatment for the patient.

Figure 3A:
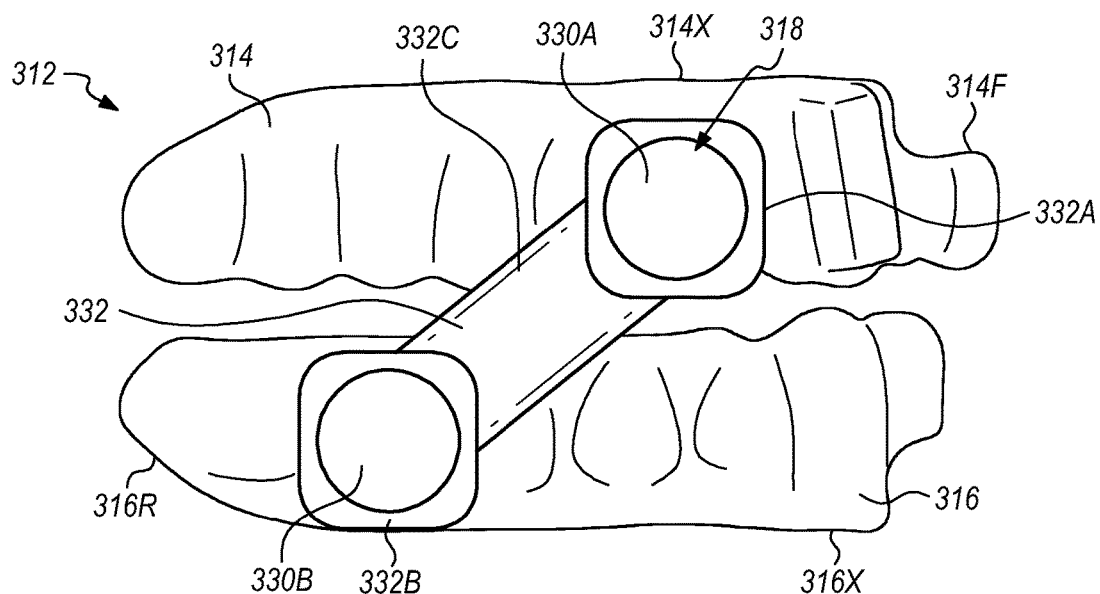
FIG. 3A is a simplified side view illustration of another embodiment of the oral appliance device.

FIG. 3A is a simplified side view illustration of another embodiment of the oral appliance device 312. More specifically, in the embodiment shown in FIG. 3A, the oral appliance device 312 includes an upper appliance member 314, a lower appliance member 316, and a connector assembly 318 that selectively and movably connects the upper appliance member 314 and the lower appliance member 316 to one another. In certain non-exclusive alternative embodiments, the oral appliance device 312 can further include one or more of the teeth spacing assembly 220 (illustrated in FIG. 2A), the nasal dilator assembly 422 (illustrated in FIG. 4A), the tongue positioner assembly 524 (illustrated in FIG. 5A) and the jaw position controller 626 (illustrated in FIG. 6A).

As with the previous embodiments, as well as all other embodiments illustrated and described herein, during use of the oral appliance device 312, the upper appliance member 314 is positioned to selectively engage the upper teeth 11A (illustrated in FIG. 1) and the lower appliance member 316 is positioned to selectively engage the lower teeth 11B (illustrated in FIG. 1).

The connector assembly 318 can have any suitable design. As illustrated in this embodiment, the connector assembly 318 includes (i) a first connector button 330A that is removably secured to the upper appliance member 314, i.e. toward a front 314F of the upper appliance member 314; (ii) a second connector button 330B that is removably secured to the lower appliance member 316, i.e. toward a rear 316R of the lower appliance member 316; and (iii) a connector band 332 that is selectively secured or coupled to each of the upper appliance member 314 (i.e. via the first connector button 330A) and the lower appliance member 316 (i.e. via the second connector button 330B). It is appreciated that with the connector band 332 being secured or coupled to the upper appliance member 314 toward the front 314F of the upper appliance member 314 and being secured or coupled to the lower appliance member 316 toward the rear 316R of the lower appliance member 316, the connector band 332 is able to inhibit the lower teeth 11B (and the lower jaw 17B (illustrated in FIG. 1)) from falling back in a supine position and potentially blocking the upper airway of the individual.

In various embodiments, the first connector button 330A and the second connector button 330B can be formed from any suitable materials and/or can be formed from any suitable manufacturing process. For example, in some non-exclusive embodiments, each of the connector buttons 330A, 330B can be formed from a nylon-based material, e.g., PA 2200 nylon, polyamide 12 nylon, or another suitable nylon material. Alternatively, each of the connector buttons 330A, 330B can be formed from other suitable materials.

Additionally, in certain non-exclusive alternative embodiments, each of the connector buttons 330A, 330B can be manufactured using one of a three-dimensional printer and a selective laser sintering process. With such design, each of the connector buttons 330A, 330B can be quickly and easily made or remade from a single model without the need for additional impressions or models. Alternatively, each of the connector buttons 330A, 330B can be manufactured using another suitable process.

As noted, the connector band 332 is selectively secured or coupled to each of the upper appliance member 314 (i.e. via the first connector button 330A) and the lower appliance member 316 (i.e. via the second connector button 330B). The connector band 332 can have any suitable design for purposes of selectively and movably coupling the upper appliance member 314 and the lower appliance member 316. In some embodiments, the connector band 332 can be elastic to allow for minimized relative movement or retrusion between the jaws. In other embodiments, the connector band 332 can be more rigid. In the embodiment illustrated in FIG. 3A, the connector band 332 includes a first band end 332A that is selectively secured or coupled to the upper appliance member 314, a second band end 332B that is selectively secured or coupled to the lower appliance member 316, and an elongated, band body 332C that extends between the first band end 332A and the second band end 332B.

As shown, each of the first band end 332A and the second band end 332B can be substantially rectangle-shaped or square-shaped. As such, each of the first band end 332A and the second band end 332B include at least two substantially linear edges that are at an angle, e.g., substantially perpendicular, relative to one another. Additionally, as illustrated, the connector band 332 is uniquely configured such that the first band end 332A does not extend above an upper extreme, or upper edge 314X, of the upper appliance member 314, and the second band end 332B does not extend below a lower extreme, or lower edge 316X, of the lower appliance member 316. With such design, the connector band 332, i.e. the band ends 332A, 332B, is generally configured so as to not aggravate the lip or gum area adjacent to where the band ends 332A, 332B are secured or coupled to the upper appliance member 314 and the lower appliance member 316, respectively. Alternatively, the first band end 332A and/or the second band end 332B can have a different shape, e.g., a round shape, an oval shape, a triangle shape, a diamond shape, or another suitable shape.

The connector band 332 can be formed from any suitable materials and/or can be formed from any suitable manufacturing process. More particularly, in various embodiments, the connector band 332 can be composed of materials having different shoreness and flexibility profiles, each having different characteristics, features, and benefits. Additionally, different wear rates can be provided for with different materials and compositions for the connector band 332. As such, the connector band 332 can enable the healthcare professional to monitor use of the connector band 332 as a feedback device. For example, if patients are wearing through the connector band 332 rapidly or frequently breaking the connector band 332, this can indicate that additional or other components may require adjustment or analysis, for example, a nasal dilator component.

In some non-exclusive embodiments, the connector band 332 can be formed from a nylon-based material, e.g., PA 2200 nylon, polyamide 12 nylon, or another suitable nylon material. Alternatively, in another embodiment, the connector band 332 can be formed from an elastomeric material, such as medium-grade santoprene. Still alternatively, the connector band 332 can be formed from one or more materials or compositions such as silicone, elastosil, rubber, and others that provide some amount of flexibility. Yet alternatively, the connector band 332 can be formed from other suitable materials.

Additionally, in certain non-exclusive alternative embodiments, the connector band 332 can be manufactured using one of a three-dimensional printer and a selective laser sintering process. Alternatively, the connector band 332 can be manufactured using another suitable process.

Figure 3B:
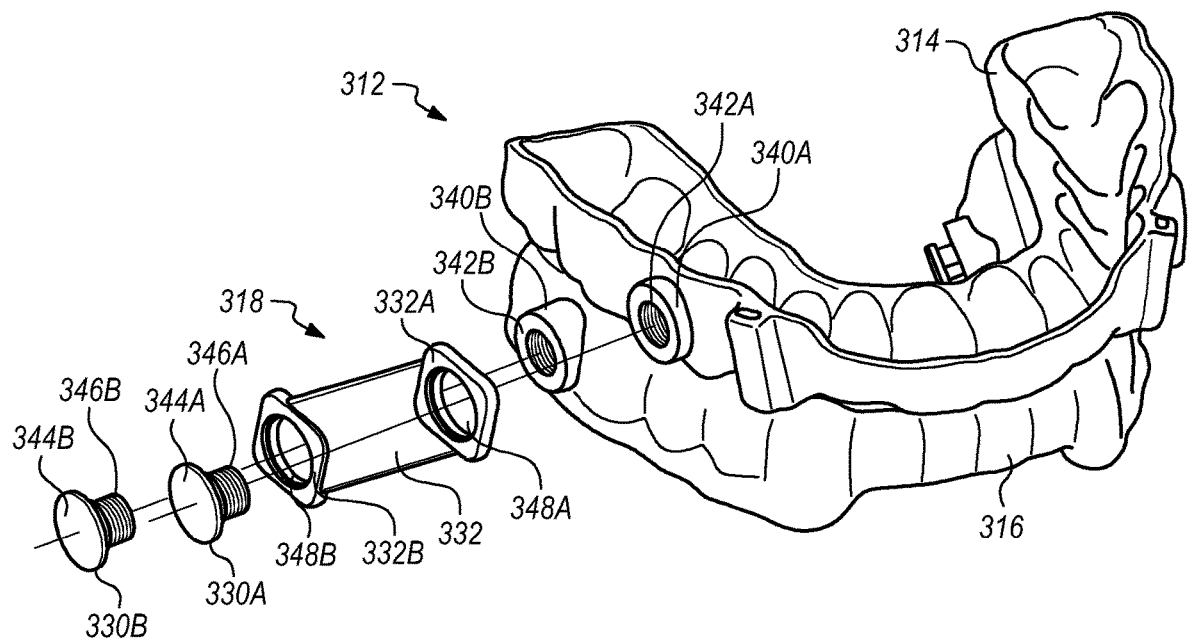
FIG. 3B is a partially exploded view illustration of the oral appliance device illustrated in FIG. 3A.

FIG. 3B is a partially exploded view illustration of the oral appliance device 312 illustrated in FIG. 3A. In particular, FIG. 3B illustrates details of the connector assembly 318 that shows how the connector assembly 318 and/or the connector band 332 can be selectively and removably secured to the upper appliance member 314 and the lower appliance member 316.

As shown in FIG. 3B, in addition to the connector buttons 330A, 330B and the connector band 332, the connector assembly 318 further includes a first connector base 340A that is secured to and/or integrally formed with the upper appliance member 314, and a second connector base 340B that is secured to and/or integrally formed with the lower appliance member 316. In some embodiments, the first connector base 340A can include a first base aperture 342A that is internally threaded; and the second connector base 340B can include a second base aperture 342B that is also internally threaded.

Additionally, in this embodiment, the first connector button 330A includes a first button head 344A and a first button shaft 346A that extends away from the first button head 344A. As illustrated, the first button shaft 346A can include external threads that are configured to threadingly engage the internal threads of the first base aperture 342A of the first connector base 340A. Similarly, the second connector button 330B includes a second button head 344B and a second button shaft 346B that extends away from the second button head 344B As illustrated, the second button shaft 346B can include external threads that are configured to threadingly engage the internal threads of the second base aperture 342B of the second connector base 340B.

Further, as shown, the first band end 332A of the connector band 332 includes a first band aperture 348A, and the second band end 332B of the connector band 332 includes a second band aperture 348B.

With the design of the connector assembly 318 as described in detail herein, the connector band 332 and/or the connector buttons 330A, 330B can be removably secured to the upper appliance member 314 and the lower appliance member 316. More specifically, when it is desired to couple the connector band 332 to the upper appliance member 314, the externally threaded first connector shaft 346A of the first connector button 330A is extended through the first band aperture 348A of the first band end 332A of the connector band 332 and is threaded into the first base aperture 342A of the first connector base 340A. Thus, the first connector button 330A is threadingly secured or coupled to the upper appliance member 314, and the connector band 332 is thus selectively secured or coupled to the upper appliance member 314 via the first connector button 330A that is removably secured to the upper appliance member 314. Similarly, when it is desired to couple the connector band 332 to the lower appliance member 316, the externally threaded second connector shaft 346B of the second connector button 330B is extended through the second band aperture 348B of the second band end 332B of the connector band 332 and is threaded into the second base aperture 342B of the second connector base 340B. Thus, the second connector button 330B is threadingly secured or coupled to the lower appliance member 316, and the connector band 332 is thus selectively secured or coupled to the lower appliance member 316 via the second connector button 330B that is removably secured to the lower appliance member 316.

Figure 4A:
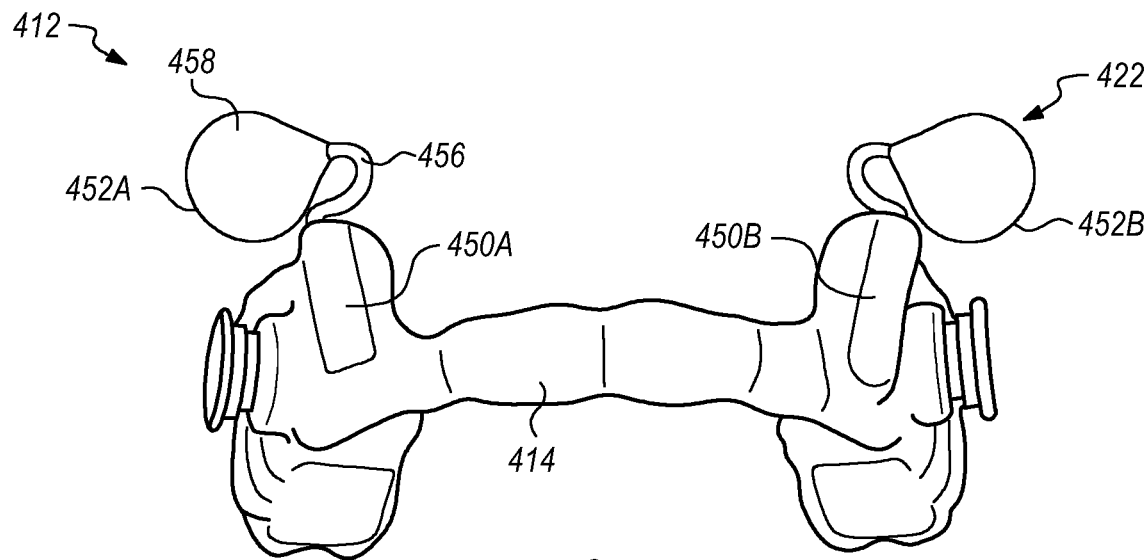
FIG. 4A is a simplified perspective view illustration of still another embodiment of the oral appliance device.

FIG. 4A is a simplified perspective view illustration of still another embodiment of the oral appliance device 412. In particular, FIG. 4A illustrates the oral appliance device 412 including the upper appliance member 414, and an embodiment of the nasal dilator assembly 422 that is secured or coupled to the upper appliance member 414. The lower appliance member is not illustrated in FIG. 4A for purposes of clarity, as the nasal dilator assembly 422, as noted, is specifically secured or coupled to the upper appliance member 414. However, it is appreciated that this embodiment of the oral appliance device 412 will also typically include the lower appliance member. Additionally, in certain non-exclusive alternative embodiments, the oral appliance device 412 can further include one or more of the teeth spacing assembly 220 (illustrated in FIG. 2A), the connector assembly 318 (illustrated in FIG. 3A), the tongue positioner assembly 524 (illustrated in FIG. 5A), the jaw position controller 626 (illustrated in FIG. 6A), and the Herbst device assembly 728 (illustrated in FIG. 7A).

As with the other embodiments, during use of the oral appliance device 412, the upper appliance member 414 is sized, shaped and positioned to selectively engage the upper teeth 11A (illustrated in FIG. 1). As shown, the upper appliance member 414 can include a molding or casting of the patient's upper teeth 11A and a portion of surrounding oral geography. The molding or casting of the upper teeth 11A can be taken in any suitable manner. For example, one type of molding can include taking images of a patient's oral anatomy with a digital scanner or from impressions using a computer to map them before fabricating a molding. Additionally, in certain non-exclusive alternative embodiments, the upper appliance member 414 can then be manufactured using one of a three-dimensional printer and a selective laser sintering process. Intraoral scanners can allow patient information to be captured and stored in digital format before being transmitted or otherwise delivered to the three-dimensional printer or the selective laser sintering device for fabrication. Further, it is appreciated that in embodiments that also include the lower appliance member, the lower appliance member can be formed in a similar manner. Still further, it is also appreciated that in certain embodiments, the upper appliance member 414 (and the lower appliance member) can be formed from any suitable nylon-based materials.

The nasal dilator assembly 422 is configured to dilate the nasal passage of the patient, thereby improving airflow through the nasal-pharyngeal passageways. Additionally, in this embodiment, the nasal dilator assembly 422 is configured to dilate the nasal passage of the patient while being positioned entirely within the oral cavity of the patient. The design of the nasal dilator assembly 422 can be varied to suit the requirements of the oral appliance device 412 and/or the specific needs of the patient. In certain embodiments, as shown in FIG. 4A, the nasal dilator assembly includes a first dilator receiver 450A, a second dilator receiver 450B, a first nasal dilator 452A that is removably and adjustably secured or coupled to the first dilator receiver 450A, and a second nasal dilator 452B that is removably and adjustably secured or coupled to the second dilator receiver 450B. Alternatively, the nasal dilator assembly 422 can include more components or fewer components than those specifically illustrated and described herein. For example, in one non-exclusive alternative embodiment, the nasal dilator assembly 422 need only include one dilator receiver 450A, 450B and one nasal dilator 452A, 452B that is removably and adjustably secured or coupled to the one dilator receiver 450A, 450B.

In one embodiment, each of the first dilator receiver 450A and the second dilator receiver 450B are integrally formed with the upper appliance member 414 during manufacturing of the upper appliance member 414. Alternatively, in another embodiment, the first dilator receiver 450A and/or the second dilator receiver 450B can be manufactured independently, and can then be permanently or removably affixed, attached, secured, connected or otherwise secured or coupled to the upper appliance member 414 during a post-manufacturing process.

Additionally, the first dilator receiver 450A is configured to hold or maintain the first nasal dilator 452A in a fixed or minimally movable position when the first nasal dilator 452A is selectively (and removably) secured or coupled to the first dilator receiver 450A. Similarly, the second dilator receiver 450B is configured to hold or maintain the second nasal dilator 452B in a fixed or minimally movable position when the second nasal dilator 452B is selectively (and removably) secured or coupled to the second dilator receiver 450B.

Figure 4B:
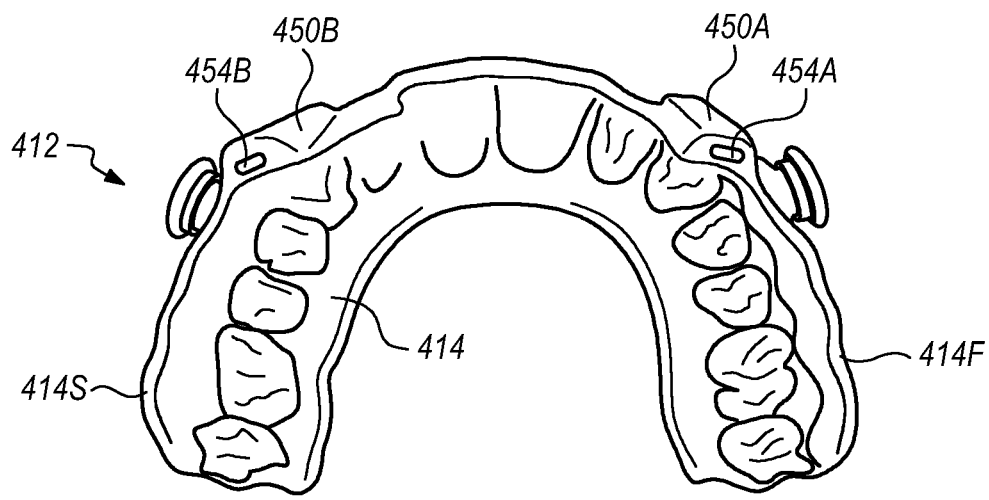
FIG. 4B is a simplified top view illustration of a portion of the oral appliance device illustrated in FIG. 4A.

Referring briefly to FIG. 4B. FIG. 4B is a simplified top view illustration of a portion of the oral appliance device 412 illustrated in FIG. 4A. More specifically, FIG. 4B illustrates the upper appliance member 414, and further illustrates details of the first dilator receiver 450A and the second dilator receiver 450B, which are secured to and/or integrally formed with the upper appliance member 414.

As shown in FIG. 4B, the first dilator receiver 450A includes a first receiver channel 454A that is configured to selectively and removably receive and retain a portion of the first nasal dilator 452A (illustrated in FIG. 4A). The first receiver channel 454A can have a generally constant rectangular, square, v-shaped, semicircular or other cross-sectional profile with one or more walls creating sides of the first receiver channel 454A. Additionally, the first receiver channel 454A can be open at one or more locations. For example, as shown in FIG. 4B, the first receiver channel 454A is open at an upper location of the first dilator receiver 450A, with the opening being located between the upper lip and gums of the patient. Further, the first receiver channel 454A can be configured to extend substantially vertically or at various angles as it extends downward within the first dilator receiver 450A. While the walls of the first receiver channel 454A can generally retain the portion of the first nasal dilator with frictional resistance, in some embodiments, the first receiver channel 454A can include securing components, e.g., ledges, ridges, latches, flaps, etc., in various locations so that the portion of the first nasal dilator 452A can be more effectively retained therein.

Similarly, the second dilator receiver 450B includes a second receiver channel 454B that is configured to selectively and removably receive and retain a portion of the second nasal dilator 452B (illustrated in FIG. 4A). The second receiver channel 454B can have a generally constant rectangular, square, v-shaped, semicircular or other cross-sectional profile with one or more walls creating sides of the second receiver channel 454B. Additionally, the second receiver channel 454B can be open at one or more locations. For example, as shown in FIG. 4B, the second receiver channel 454B is open at an upper location of the second dilator receiver 450B, with the opening being located between the upper lip and gums of the patient. Further, the second receiver channel 454B can be configured to extend substantially vertically or at various angles as it extends downward within the second dilator receiver 450B. While the walls of the second receiver channel 454B can generally retain the portion of the first nasal dilator with frictional resistance, in some embodiments, the second receiver channel 454B can include securing components, e.g., ledges, ridges, latches, flaps, etc., in various locations so that the portion of the second nasal dilator 452B can be more effectively retained therein.

Additionally, in some embodiments, the first dilator receiver 450A and/or the first receiver channel 454A can be located on a frontal surface of the upper appliance member 414, exterior to a tooth bed, and along and/or near a first side 414F of the upper appliance member 414. The first dilator receiver 450A and/or the first receiver channel 454A can further have a slope of between approximately forty-five degrees and sixty degrees from a plane across the upper teeth 11A (illustrated in FIG. 1), and may be positioned so that it slopes downward toward a central location of the upper appliance member 414 between the central incisors and angles upward toward the buccal sulcus 13 (illustrated in FIG. 1). More particularly, in one such embodiment, the first dilator receiver 450A and/or the first receiver channel 454A can begin in front of a canine or incisor and end in front of a lateral incisor facing the buccal sulcus 13.

Similarly, in some embodiments, the second dilator receiver 450B and/or the second receiver channel 454B can be located on a frontal surface of the upper appliance member 414, exterior to a tooth bed, and along and/or near a second side 414S of the upper appliance member 414. The second dilator receiver 450B and/or the second receiver channel 454B can further have a slope of between approximately forty-five degrees and sixty degrees from a plane across the upper teeth 11A, and may be positioned so that it slopes downward toward a central location of the upper appliance member 414 between the central incisors and angles upward toward the buccal sulcus 13. More particularly, in one such embodiment, the second dilator receiver 450B and/or the second receiver channel 454B can begin in front of a canine or incisor and end in front of a lateral incisor facing the buccal sulcus 13.

In various embodiments, the first dilator receiver 450A and the second dilator receiver 450B can be formed from any suitable materials and/or can be formed from any suitable manufacturing process. For example, in some non-exclusive embodiments, each of the dilator receivers 450A, 450B can be formed from a nylon-based material, e.g., PA 2200 nylon, polyamide 12 nylon, or another suitable nylon material. Alternatively, each of the dilator receivers 450A, 450B can be formed from other suitable materials.

Additionally, in certain non-exclusive alternative embodiments, each of the dilator receivers 450A, 450B can be manufactured using one of a three-dimensional printer and a selective laser sintering process. With such design, each of the dilator receivers 450A, 450B can be quickly and easily made or remade from a single model without the need for additional impressions or models. Alternatively, each of the dilator receivers 450A, 450B can be manufactured using another suitable process.

Referring back to FIG. 4A, as shown, the first nasal dilator 452A is removably secured or coupled to the first dilator receiver 450A and thus the upper appliance member 414, i.e. with a portion of the first nasal dilator 452A removably retained within the first receiver channel 454A (illustrated in FIG. 4B); and the second nasal dilator 452B is removably secured or coupled to the second dilator receiver 450B and thus the upper appliance member 414, i.e. with a portion of the second nasal dilator 452B removably retained within the second receiver channel 454B (illustrated in FIG. 4B). With the nasal dilators 452A, 452B so secured or coupled to the dilator receivers 450A, 450B, the nasal dilators 452A, 452B can be selectively and adjustably positioned to push the upper lip of the patient into a position that is located away and spaced apart from the maxillary dental arch of the patient. When properly positioned, the nasal dilators 452A, 452B can effectively dilate the nasal passage of the patient, thereby improving airflow through the nasal-pharyngeal airways.

It is appreciated that each of the first nasal dilator 452A and the second nasal dilator 452B can be substantially similar in design and function. However, with the modular design of the nasal dilators 452A, 452B, as described in detail herein, it is further appreciated that the specific dimensions and positioning of any components of the nasal dilators 452A, 452B can be varied to suit the particular anatomical requirements of the patient with whom the nasal dilator assembly 422 is being used. In various embodiments, each of the nasal dilators 452A, 452B can include a dilator positioner 456, e.g., a wire, and a dilator bulb 458 that is removably or permanently secured or coupled to the dilator positioner 456.

Figure 4C:
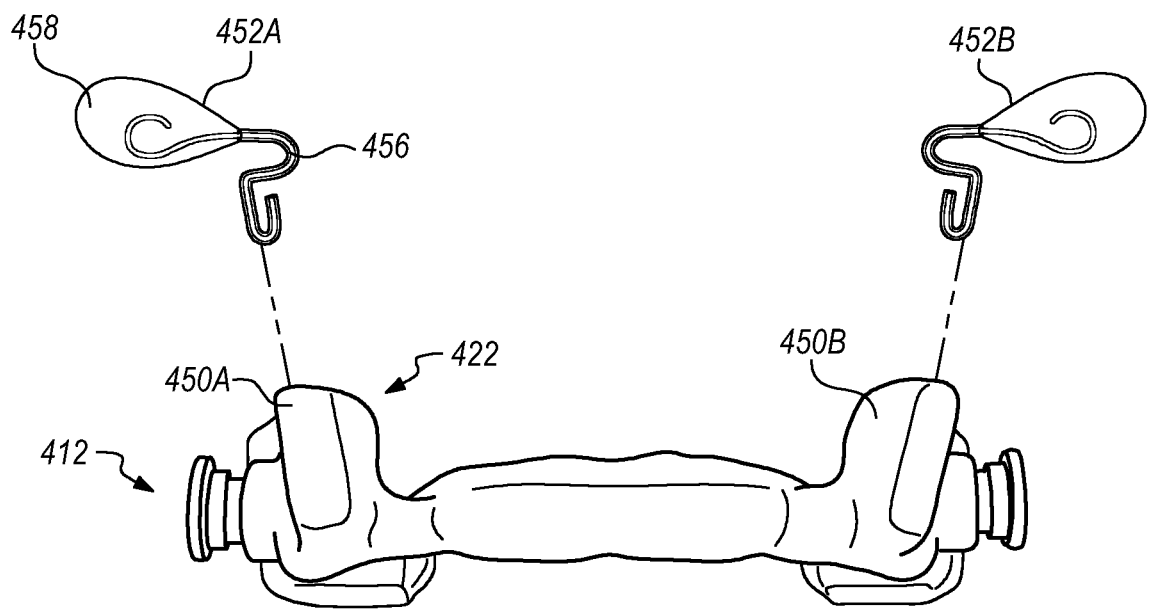
FIG. 4C is a partially exploded view illustration of a portion of the oral appliance device illustrated in FIG. 4A.

Referring now to FIG. 4C, FIG. 4C is a partially exploded view illustration of a portion of the oral appliance device 412 illustrated in FIG. 4A. In particular, FIG. 4C illustrates the nasal dilator assembly 422 with the nasal dilators 452A, 452B being spaced apart from the dilator receivers 450A, 450B, respectively.

In various embodiments, the dilator positioner 456 is flexible and/or bendable such that the dilator positioner 456 can be maneuvered and manipulated as desired to enable better and/or more precise positioning of the dilator bulb 458. Additionally, the dilator positioner 456 is configured to extend into and be removably retained within the receiver channel 454A. 454B (illustrated in FIG. 4B) of the dilator receiver 450A, 450B. In some embodiments, the walls of the receiver channel 454A, 454B can provide frictional resistance to the dilator positioner 456 that is positioned within the receiver channel 454A, 454B to inhibit the nasal dilator 452A, 452B from becoming dislodged from the body of the upper appliance member 414. Further, with the flexibility of the dilator positioner 456, frictional resistance within the receiver channel 454A, 454B to movement of the dilator positioner 456 can be increased or decreased by modifying, manipulating, or moving one or more bends or loops of the dilator positioner 456 closer together or farther apart. With the dilator positioner 456 effectively retained within the receiver channel 454A, 454B, the dilator bulb 458 can then be maintained in a fixed or semi-fixed position, as desired, with respect to the upper appliance member 414. Additionally, it is appreciated that with the maneuverability and flexibility of the dilator positioner 456, the nasal dilator 452A, 452B can be easily removed from the receiver channel 454A, 454B if necessary to adjust the nasal dilator 452A, 452B for improved functionality or replacement.

The dilator positioner 456 can be of any suitable size and can formed from any suitable materials. For example, in certain embodiments, the dilator positioner 456 can be formed from stainless steel and can have a circular cross-section that is between approximately 0.03 millimeters and 0.04 millimeters in diameter. Alternatively, the dilator positioner 456 can have a different size and shape, and/or the dilator positioner 456 can be formed from any other suitable materials.

As noted above, in alternative embodiments, the dilator bulb 458 can be removably or permanently secured or coupled to the dilator positioner 456. Additionally, with the flexibility of the dilator positioner 456, the dilator bulb 458 can be better positioned as desired. More particularly, the dilator bulb 458 can be rotated and repositioned, anteriorly, posteriorly, laterally, or in other directions, by manipulating and changing the angle of the dilator positioner 456. As such, the dilator positioner 456 can maintain the dilator bulb 458 in a fixed or semi-fixed position with respect to the upper appliance member 414, thus inhibiting any undesired movement of the dilator bulb 458 relative to the upper appliance member 414, even if the patient moves. Thus, the patient and/or the healthcare professional are able to freely move, adjust, remove, and otherwise adjust or manipulate the dilator bulb 458 as necessary.

The dilator bulb 458 can have any suitable design. For example, in some non-exclusive embodiments, the dilator bulb 458 can be generally planar and/or can be somewhat cylindrical-shaped, conical-shaped, spherical-shaped, tear drop-shaped, or another suitable regular or irregular shape.

Additionally, the dilator bulb 458 can be designed to have any desired shore hardness and rigidity, and can be of any suitable size. For example, in certain embodiments, the dilator bulb 458 can be modified between soft, medium and hard firmness, and the size can be modified between small, medium and large in varying degrees. As such, the healthcare professional can select an appropriate nasal dilator 452A, 452B and/or an appropriate dilator bulb 458 from a plurality of alternative nasal dilators, where each nasal dilator has a certain degree of freedom of movement for correct positioning according to the unique anatomy of each individual patient. Thus, the healthcare professional is better able to attend to and address the needs of each patient individually. Additionally, different nasal dilator sizes can be considered when selecting an appropriate nasal dilator, and a nasal dilator can be easily exchanged if improper or undesired results are likely to occur, thus optimizing treatments on a per patient basis.

Further, with the noted flexibility of the dilator positioner 456, by modifying, manipulating or moving bends or loops of the dilator positioner 456, the dilator bulb 458 can be positioned to allow the dilator bulb 458 to provide increased or decreased resistance to lip, nasal or other nearby structures when adjusted. Thus, the dilator bulb 458 can be positioned in any suitable manner, as desired, within the oral cavity of the patient, to provide the desired treatment options for the patient.

The dilator bulb 458 can be formed from any suitable materials. For example, in one embodiment, the dilator bulb 458 can be formed from a nylon-based material, e.g., PA 2200 nylon, polyamide 12 nylon, or another suitable nylon material. Alternatively, in another embodiment, e.g., when soft firmness is desired, the dilator bulb 458 can be formed from an organic compound such as ethyl-methacrylate. Still alternatively, in still another embodiment, e.g., when hard firmness is desired, the dilator bulb 458 can be formed from an organic compound such as methyl-methacrylate. Yet alternatively, the dilator bulb 458 can be formed from other suitable materials.

Additionally, in certain non-exclusive alternative embodiments, the dilator bulb 458 can be manufactured using one of a three-dimensional printer and a selective laser sintering process. Alternatively, the dilator bulb 458 can be manufactured using another suitable process.

Figure 5A:
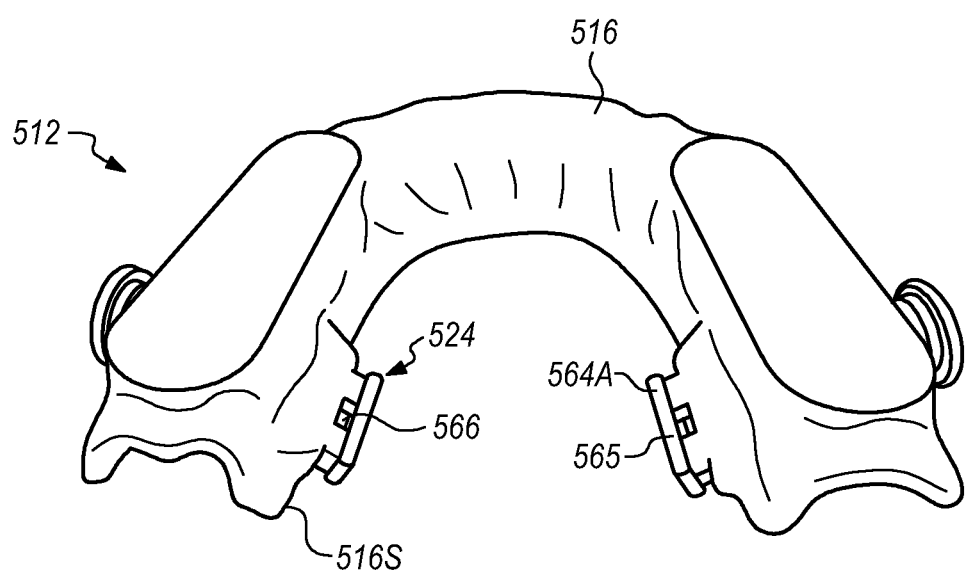
FIG. 5A is a simplified top perspective view illustration of another embodiment of the oral appliance device.

FIG. 5A is a simplified top perspective view illustration of another embodiment of the oral appliance device 512. In particular, FIG. 5A illustrates the oral appliance device 512 including the lower appliance member 516, and an embodiment of the tongue positioner assembly 524 that is secured or coupled to the lower appliance member 516. The upper appliance member is not illustrated in FIG. 5A for purposes of clarity, as the tongue positioner assembly 524, as noted, is specifically secured or coupled to the lower appliance member 516. However, it is appreciated that this embodiment of the oral appliance device 512 will also typically include the upper appliance member. Additionally, in certain non-exclusive alternative embodiments, the oral appliance device 512 can further include one or more of the teeth spacing assembly 220 (illustrated in FIG. 2A), the connector assembly 318 (illustrated in FIG. 3A), the nasal dilator assembly 422 (illustrated in FIG. 4A), the jaw position controller 626 (illustrated in FIG. 6A), and the Herbst device assembly 728 (illustrated in FIG. 7A).

As with the other embodiments, during use of the oral appliance device 512, the lower appliance member 516 is sized, shaped and positioned to selectively engage the lower teeth 11B (illustrated in FIG. 1). As shown, the lower appliance member 516 can include a molding or casting of the patient's lower teeth 11B and a portion of surrounding oral geography. The molding or casting of the lower teeth 11B can be taken in any suitable manner. For example, one type of molding can include taking images of a patient's oral anatomy with a digital scanner or from impressions using a computer to map them before fabricating a molding. Additionally, in certain non-exclusive alternative embodiments, the lower appliance member 516 can then be manufactured using one of a three-dimensional printer and a selective laser sintering process. Intraoral scanners can allow patient information to be captured and stored in digital format before being transmitted or otherwise delivered to the three-dimensional printer or the selective laser sintering device for fabrication. Further, it is appreciated that in embodiments that also include the upper appliance member, the upper appliance member can be formed in a similar manner. Still further, it is also appreciated that in certain embodiments, the lower appliance member 516 (and the upper appliance member) can be formed from any suitable nylon-based materials.

The tongue positioner assembly 524 is configured to adjust the position of the tongue 15 (illustrated in FIG. 1) within the mouth 10 (illustrated in FIG. 1) of the patient. More specifically, in various embodiments, the tongue positioner assembly 524 is configured to pull the base of the tongue 15 of the patient forward, thus repositioning the lower jaw 17B (illustrated in FIG. 1) and tongue 15 of the patient in an anterior position. Thus, the tongue positioner assembly 524 can increase the area available for air passage in the posterior pharyngeal region, thereby opening the breathing passage behind the tongue 15 and improving patient respiration.

Additionally, as provided herein, the tongue positioner assembly 524 can have a modular design that incorporates one or more tongue positioners 560 (illustrated in FIG. 5B), which can be selectively, alternatively and removably attached to the lower appliance member 516 within the mouth 10 of the patient. For example, in many embodiments, the tongue positioner assembly 524 and/or the oral appliance device 512 includes a tongue positioner 560 that is alternatively and removably attached to an inner surface 516S on either side of the lower appliance member 516. Additionally, each tongue positioner 560 can have any suitable size and shape, and can be positioned with any desired orientation within the mouth 10 of the patient. Stated in another manner, the tongue positioner assembly 524 enables the healthcare professional and/or the patient to select from a wide variety of alternative options for the specific design and positioning of the tongue positioner 560. Thus, with the multitude of available alternative options for the specific design and orientation of the tongue positioner 560, the healthcare professional is better able to alleviate snoring and other sleep-related problems for his or her patients, as compared with current non-invasive treatment methods and invasive treatment methods including surgery.

The design of the tongue positioner assembly 524 can be varied to suit the specific requirements of the oral appliance device 512 and/or the specific anatomical requirements of the patient with whom the tongue positioner assembly 524 is being used. In various embodiments, the tongue positioner assembly 524 includes one or more tongue positioners 560, with the lower appliance member 516 including a positioner receiver 564A and with each of the one or more tongue positioners including an appliance engager 564B (illustrated in FIG. 5B) for selectively and removably attaching the tongue positioners 560 to the inner surface 516S on either side of the lower appliance member 516. Alternatively, the tongue positioner assembly 524 can include more components or fewer components than those illustrated and described herein, and/or the specific design of the tongue positioners 560 and the lower appliance member 516 can be different than what is illustrated and described herein.

Figure 5B:
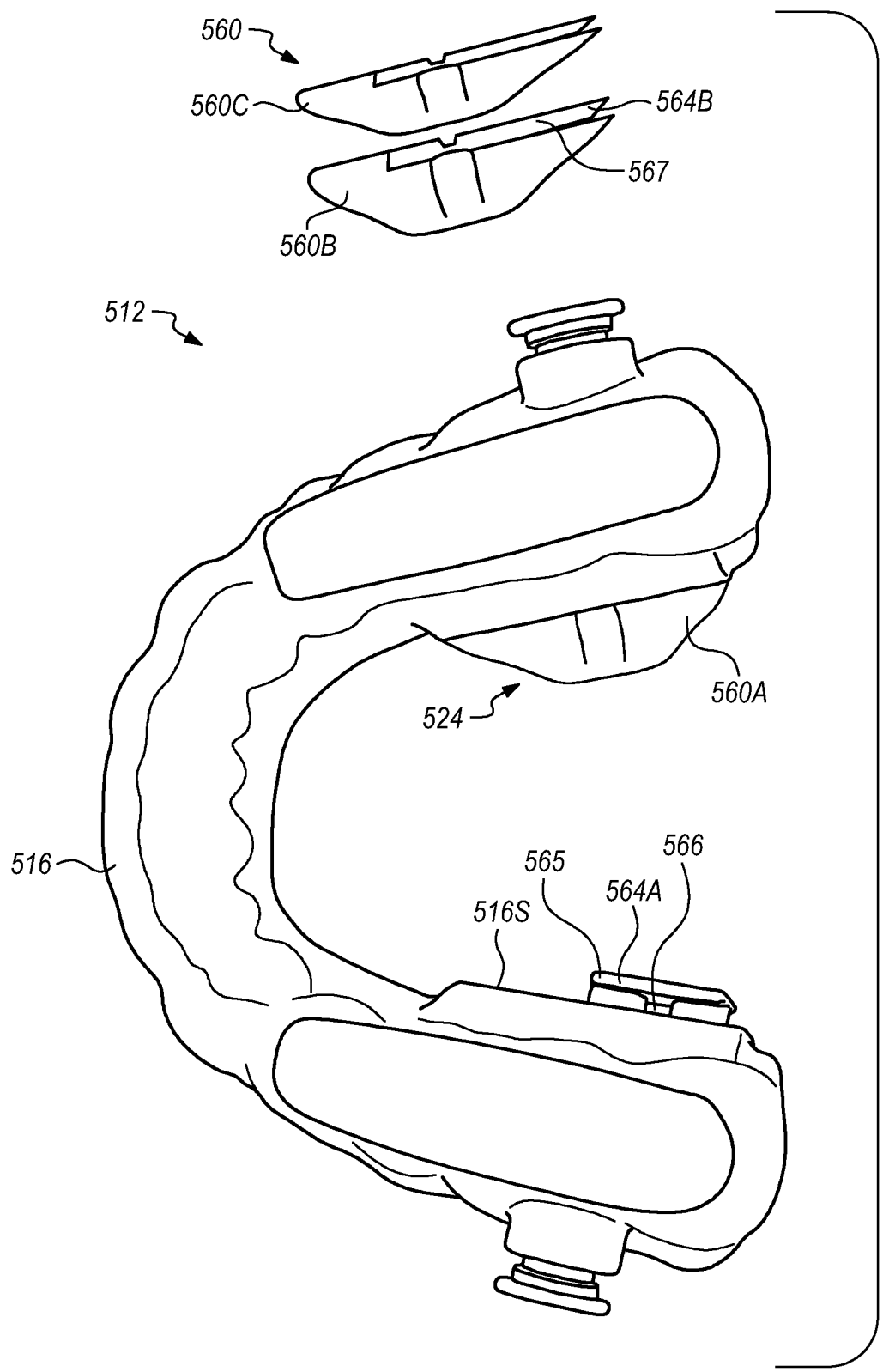
FIG. 5B is a partially exploded view illustration of the oral appliance device illustrated in FIG. 5A.

Referring now to FIG. 5B, FIG. 5B is a partially exploded view illustration of the oral appliance device 512 illustrated in FIG. 5A. Additionally, FIG. 5B illustrates that the tongue positioners 560 that are usable as part of the tongue positioner assembly 524 can have any suitable size, shape and orientation when used and positioned as desired within the mouth 10 (illustrated in FIG. 1) of the patient. More specifically, FIG. 5B illustrates a first tongue positioner 560A that has already been removably attached to the lower appliance member 516, and a second tongue positioner 560B and a third tongue positioner 560C that can additionally and/or alternatively be removably attached to the lower appliance member 516. As provided herein, each of the tongue positioners 560A, 560B, 560C can have a different size and/or shape. Alternatively, one or more of the tongue positioners 560A, 560B, 560C can be substantially similar in shape.

In certain embodiments, the tongue positioner 560 can have dimensions including a length that is between approximately ten millimeters and thirteen millimeters, a width that is between approximately five millimeters and seven millimeters, and a thickness that is between approximately four millimeters and six millimeters. Alternatively, in other embodiments, the tongue positioner 560 can have dimensions including a length that is between approximately eighteen millimeters and twenty-one millimeters, a width that is between approximately five millimeters and seven millimeters, and a thickness that is between approximately four millimeters and six millimeters. Still alternatively, in still other embodiments, the tongue positioner 560 can have dimensions where the length, the width and/or the thickness are different than the specific examples listed herein above.

In various embodiments, each of the tongue positioners 560 can be formed from any suitable materials and/or can be formed from any suitable manufacturing process. For example, in some non-exclusive embodiments, each of the tongue positioners 560 can be formed from a nylon-based material, e.g., PA 2200 nylon, polyamide 12 nylon, or another suitable nylon material. Alternatively, each of the tongue positioners 560 can be formed from other suitable materials.

Additionally, in certain non-exclusive alternative embodiments, each of the tongue positioners 560 can be manufactured using one of a three-dimensional printer and a selective laser sintering process. With such design, each of the tongue positioners 560 can be quickly and easily made or remade from a single model without the need for additional impressions or models. Alternatively, each of the tongue positioners 560 can be manufactured using another suitable process.

The tongue positioners 560 and/or the lower appliance member 516 can include any suitable design features for purposes of selectively and removably attaching the tongue positioner 560 to the lower appliance member 516. For example, as noted above and as shown more clearly in FIG. 5A, the lower appliance member 516 can include a pair of positioner receivers 564A for purposes of selectively and removably attaching one of the tongue positioners 560 to the inner surface 516S on either side of the lower appliance member 516. Further, as noted, the use of the tongue positioners 560 allows for improved respiration for the patient by repositioning the lower jaw 17B and tongue 15 (illustrated in FIG. 1) in an interior position, thereby opening the breathing passage behind the tongue 15 to better enable the healthcare professional to alleviate snoring and other sleep-related problems for his or her patients.

In certain embodiments, each positioner receiver 564A can be integrally formed with the lower appliance member 516. Alternatively, each positioner receiver 564A can be separately formed and independently secured to the lower appliance member. Additionally, each tongue positioner 560 can include an appliance engager 564B that is integrally formed as part of the tongue positioner 560. In such embodiments, the appliance engager 564B is configured to selectively engage the positioner receiver 564A so that the tongue positioner 560 can be selectively and removably secured to the lower appliance member 516.

The positioner receiver 564A and the appliance engager 564B can have any suitable design for purposes of selectively and removably attaching the tongue positioners 560 to the lower appliance member 516. For example, in some embodiments, as shown in FIGS. 5A and 5B, the positioner receiver 564A can include and/or incorporate a generally "T-shaped" receiver extension 565 that is secured or coupled to and extends away from the inner surface 516S of the lower appliance member 516. In such embodiments, the T-shaped receiver extension 565 can be oriented such that the cross at the top is substantially parallel to the inner surface 516S of the lower appliance member 516 from which the perpendicular bottom section of the T-shaped extension 565 extends. The top of the receiver extension 565 can also be referred to herein as an "interior ridge". The interior ridge is operable to support and maintain the position of the tongue positioner 560 relative to the lower appliance device 516. Additionally, in certain embodiments, the positioner receiver 564A can further including a locking mechanism 566 for locking the tongue positioner 560 in position. Alternatively, the positioner receiver 564A can have another suitable design.

Additionally, in some embodiments, the appliance engager 564B can include a slot 567 with parallel and opposing sides that is configured to slide over and slidably receive and engage the interior ridge of the receiver extension 565, so that the appliance engager 564B is effectively attached to the positioner receiver 564A. In certain such embodiments, when the slot 567 of the appliance engager 564B slides over and is attached to the positioner receiver 564A, the appliance engager 564B can include one or more engager extensions (not shown) within the slot 567 that engage the locking mechanism 566 such that the tongue positioner 560 is securely, albeit removably, secured or coupled to the lower appliance member 516.

Further, in some embodiments, it is appreciated that the tongue positioners 560 can be secured or coupled to the lower appliance member 516, i.e. via the appliance engager 564B and the positioner receiver 564A, in different orientations. For example, in certain such embodiments, the tongue positioners 560 can be secured or coupled in an orientation that is angled between about forty-five degrees and sixty degrees above a horizontal plane. Additionally, in some embodiments, this can be inverted, such that the tongue positioners 560 are secured or coupled in an orientation that is angled between about forty-five degrees and sixty degrees below a horizontal plane. Other angles are also contemplated, and may be adjusted according to the anatomical arrangements of the patient.

In various embodiments, with the positioner receiver 564A being part of the lower appliance member 516 and the appliance engager 564B being part of the tongue positioner 560, it is appreciated that the positioner receiver 564A and the appliance engager 564B can be formed from any suitable materials and/or can be formed from any suitable manufacturing process, similar to what was described above for the lower appliance member 516 and the tongue positioner 560. For example, in some non-exclusive embodiments, the positioner receiver 564A and the appliance engager 564B can be formed from a nylon-based material, e.g., PA 2200 nylon, polyamide 12 nylon, or another suitable nylon material. Alternatively, the positioner receiver 564A and the appliance engager 564B 564A, 564B can be formed from other suitable materials.

Additionally, in certain non-exclusive alternative embodiments, the positioner receiver 564A and the appliance engager 564B can be manufactured using one of a three-dimensional printer and a selective laser sintering process. Alternatively, the positioner receiver 564A and the appliance engager 564B can be manufactured using another suitable process.

In summary, in various embodiments, different sizes, shapes, and types of features for the tongue positioners 560 can be used, i.e. any alternative tongue positioners 560 can be selectively and removably secured to the lower appliance device 516, as can different configurations for the positioner receiver 564A and the appliance engager 564B. These various embodiments provide healthcare professionals and patients the ability to select tongue positioners 560 that are comfortable, while providing optimal effectiveness for individual patients with unique inferior dental arch anatomical structures.

Figure 6A:
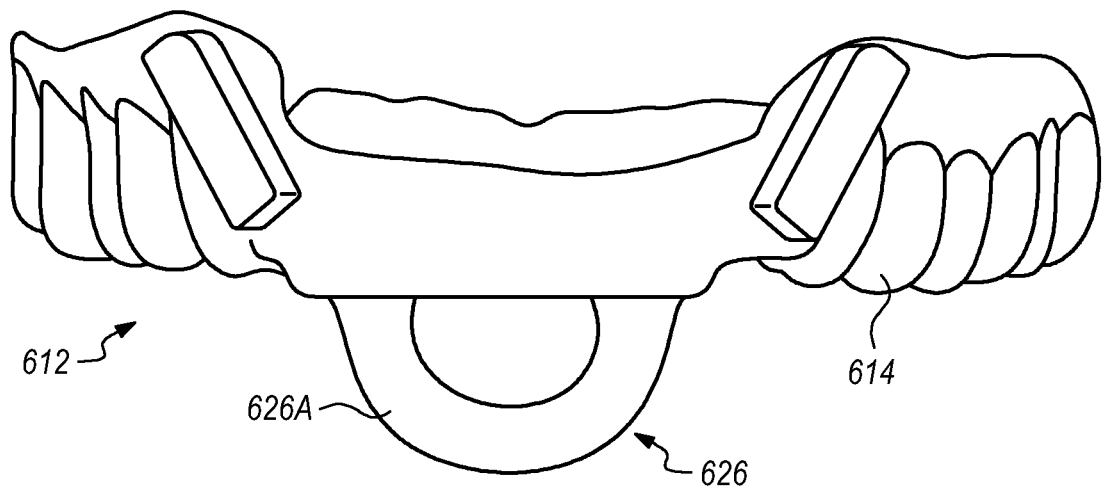
FIG. 6A is a simplified front view illustration of a portion of yet another embodiment of the oral appliance device.

FIG. 6A is a simplified front view illustration of a portion of yet another embodiment of the oral appliance device 612. In particular, FIG. 6A illustrates the oral appliance device 612 including the upper appliance member 614, and an embodiment of the jaw position controller 626 that is used with the upper appliance member 614. The lower appliance member is not illustrated in FIG. 6A for purposes of clarity, as the jaw position controller 626, as noted, is specifically used directly with the upper appliance member 614. However, it is appreciated that this embodiment of the oral appliance device 614 will also typically include the lower appliance member (e.g., the lower appliance member 316 illustrated in FIG. 3A). More specifically, during use of the oral appliance device 612 within the mouth 10 (illustrated in FIG. 1), the jaw position controller 626 is typically positioned in a manner to engage the lower appliance member. Additionally, in certain non-exclusive alternative embodiments, the oral appliance device 612 can further include one or more of the teeth spacing assembly 220 (illustrated in FIG. 2A), the connector assembly 318 (illustrated in FIG. 3A), the nasal dilator assembly 422 (illustrated in FIG. 4A), the tongue positioner assembly 524 (illustrated in FIG. 5A), and the Herbst device assembly 728 (illustrated in FIG. 7A).

As with the other embodiments, during use of the oral appliance device 612, the upper appliance member 614 is sized, shaped and positioned to selectively engage the upper teeth 11A (illustrated in FIG. 1). As shown, the upper appliance member 614 can include a molding or casting of the patient's upper teeth 11A and a portion of surrounding oral geography. The molding or casting of the upper teeth 11A can be taken in any suitable manner. For example, one type of molding can include taking images of a patient's oral anatomy with a digital scanner or from impressions using a computer to map them before fabricating a molding. Additionally, in certain non-exclusive alternative embodiments, the upper appliance member 614 can then be manufactured using one of a three-dimensional printer and a selective laser sintering process. Intraoral scanners can allow patient information to be captured and stored in digital format before being transmitted or otherwise delivered to the three-dimensional printer or the selective laser sintering device for fabrication. Further, it is appreciated that in embodiments that also include the lower appliance member, the lower appliance member can be formed in a similar manner. Still further, it is also appreciated that in certain embodiments, the upper appliance member 614 (and the lower appliance member) can be formed from any suitable nylon-based materials.

The jaw position controller 626 is configured to keep the lower jaw 17B (illustrated in FIG. 1) of the patient in a desired forward or backward position relative to the upper jaw 17A (illustrated in FIG. 1). More particularly, similar to the connector assembly 318 and the Herbst device assembly 728, the jaw position controller 626 can function as a jaw positioner to inhibit the lower teeth 11B (illustrated in FIG. 1) and the lower jaw 17B from falling back in a supine position and potentially blocking the upper airway of the patient.

The jaw position controller 626 can have any suitable design. In the embodiment illustrated in FIG. 6A, the jaw position controller 626 includes a loop 626A (or ring) or partial loop that can be provided on and extend downward from an underside of the upper appliance member 614. In one embodiment, the jaw position controller 626 is integrally formed with the upper appliance member 614. Alternatively, in another embodiment, the jaw position controller 626 can be formed separately from the upper appliance member 614 and be secured to the upper appliance member 614.

In some embodiments, the loop 626A of the jaw position controller 626 can be formed by a length of material that has a cross-sectional profile that is substantially circular. Additionally, the loop 626A can be bent such that it creates a u-shaped protuberance that extends downward at an angle from the upper appliance member 614. As such, when the oral appliance device 612 with the jaw position controller 626 is positioned in a patient's mouth, the loop 626A will rest just behind the lingual region of the lower anterior teeth 11B. Further, in such embodiments, the loop 626A is generally large enough such that it gives space for the tongue 15 (illustrated in FIG. 1) to sit, as well as increase airflow.

The jaw position controller 626, i.e. the loop 626A, can be formed from any suitable materials and can be formed in any suitable manner. Additionally, the jaw position controller 626 and/or the loop 626 can be formed so as to be flexible, semi-flexible, or rigid in certain alternative embodiments.

In certain embodiments, the jaw position controller 626 and/or the loop 626A can be formed from materials that are substantially the same as the materials utilized for the upper appliance member 614. Alternatively, the jaw position controller 626 and/or the loop 626A can be formed from materials that are different than the materials utilized for the upper appliance member 614. In some non-exclusive embodiments, the jaw position controller 626 and/or the loop 626A can be formed from a nylon-based material, e.g., PA 2200 nylon, polyamide 12 nylon, or another suitable nylon material. Alternatively, the jaw position controller 626 and/or the loop 626A can be formed from other suitable materials.

Additionally, in certain non-exclusive alternative embodiments, the jaw position controller 626 and/or the loop 626A can be manufactured using one of a three-dimensional printer and a selective laser sintering process. With such design, the jaw position controller 626 and/or the loop 626A can be quickly and easily made or remade from a single model without the need for additional impressions or models. Alternatively, the jaw position controller 626 and/or the loop 626A can be manufactured using another suitable process.

Figure 6B:
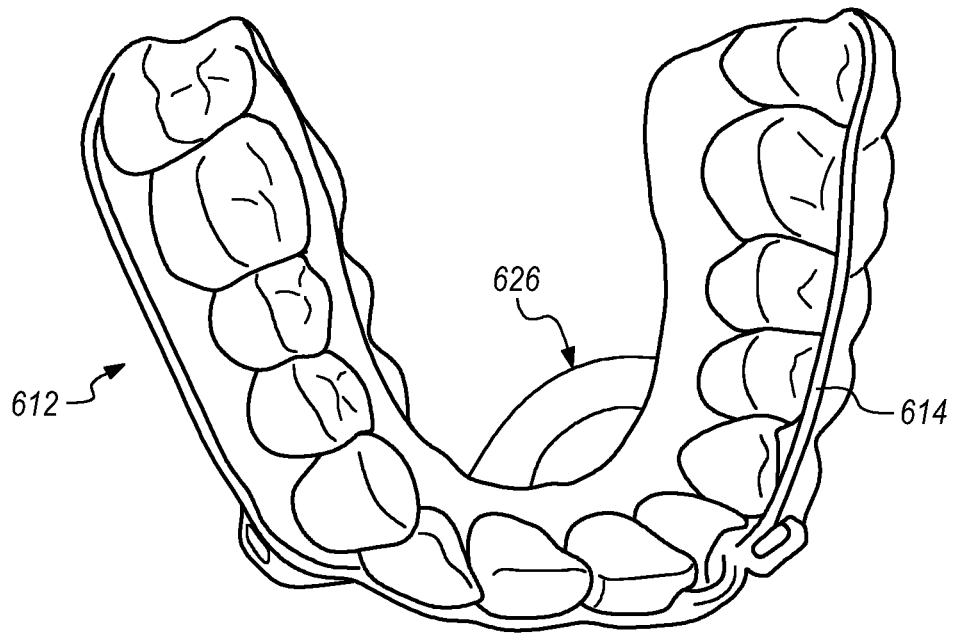
FIG. 6B is a top perspective view illustration of the portion of the oral appliance device illustrated in FIG. 6A.
Figure 6C:
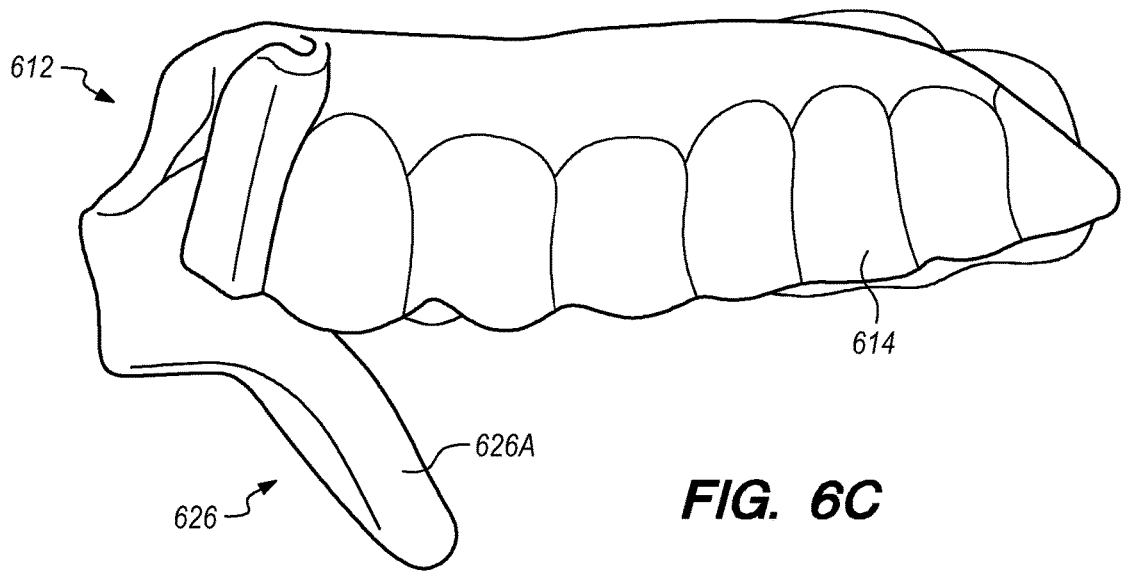
FIG. 6C is a simplified side view illustration of the portion of the oral appliance device illustrated in FIG. 6A.

FIGS. 6B and 6C provide alternative views of the portion of the oral appliance device 612 illustrated in FIG. 6A. In particular, FIG. 6B is a top perspective view illustration of the portion of the oral appliance device 612 illustrated in FIG. 6A; and FIG. 6C is a simplified side view illustration of the portion of the oral appliance device 612 illustrated in FIG. 6A. As shown, FIGS. 6B and 6C illustrate certain additional features and/or details of the jaw position controller 626 that is secured or coupled to the upper appliance member 614. For example, FIG. 6C more clearly illustrates how in certain embodiments the loop 626A extends downward and rearward at an angle from the upper appliance member 614. It is appreciated that the size of the loop 626A and the angle at which the loop 626A extends downward and rearward away from the upper appliance member 614 can be modified as desired to suit the particular anatomy and requirements of the patient with whom the jaw position controller 626 is being used. Additionally, it is also appreciated that the size of the loop 626A and the angle at which the loop 626A extends downward and rearward away from the upper appliance member 614 can be modified as desired to better enable the loop 626A to engage the lower appliance member during use within the mouth 10 (illustrated in FIG. 1).

Figure 7A:
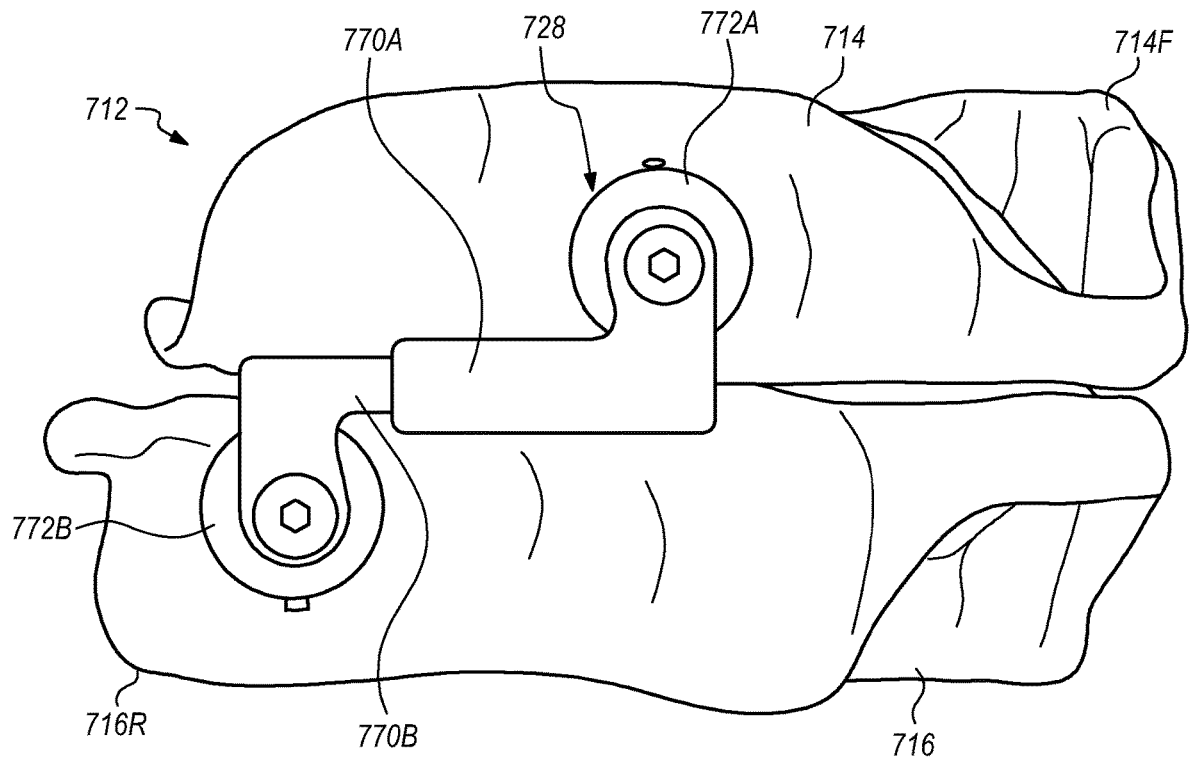
FIG. 7A is a simplified side view illustration of still yet another embodiment of the oral appliance device.

FIG. 7A is a simplified side view illustration of still yet another embodiment of the oral appliance device 712. More specifically, in the embodiment shown in FIG. 7A, the oral appliance device 712 includes an upper appliance member 714, a lower appliance member 716, and a Herbst device assembly 728 that selectively and movably couples the upper appliance member 714 and the lower appliance member 716. In certain non-exclusive alternative embodiments, the oral appliance device 712 can further include one or more of the teeth spacing assembly 220 (illustrated in FIG. 2A), the nasal dilator assembly 422 (illustrated in FIG. 4A), the tongue positioner assembly 524 (illustrated in FIG. 5A) and the jaw position controller 626 (illustrated in FIG. 6A).

As with the other embodiments, during use of the oral appliance device 712, the upper appliance member 714 is positioned to selectively engage the upper teeth 11A (illustrated in FIG. 1) and the lower appliance member 716 is positioned to selectively engage the lower teeth 11B (illustrated in FIG. 1). As shown, the upper appliance member 714 can include a molding or casting of the patient's upper teeth 11A and a portion of surrounding oral geography. Similarly, the lower appliance member 716 can include a molding or casting of the patient's lower teeth 11B and a portion of surrounding oral geography. The molding or casting of the upper teeth 11A and the lower teeth 11B can be taken in any suitable manner. For example, one type of molding can include taking images of a patient's oral anatomy with a digital scanner or from impressions using a computer to map them before fabricating a molding. Additionally, in certain non-exclusive alternative embodiments, the appliance members 714, 716 can then be manufactured using one of a three-dimensional printer and a selective laser sintering process. Intraoral scanners can allow patient information to be captured and stored in digital format before being transmitted or otherwise delivered to the three-dimensional printer or the selective laser sintering device for fabrication. Further, it is appreciated that in certain embodiments, the appliance members 714, 716 can be formed from any suitable nylon-based materials.

The Herbst device assembly 728 is configured to correct the bite, e.g., an overbite, and/or correct jaw growth discrepancies of a patient. More specifically, in various embodiments, the Herbst device assembly 728 is configured to hold the lower jaw 17B (illustrated in FIG. 1) forward and/or inhibit the lower jaw 17B from moving backward in a supine position, and encourage the lower jaw 17B to grow and catch up with the size of the upper jaw 17A (illustrated in FIG. 1) and face, thereby eliminating an overbite of the patient.

Additionally, the Herbst device assembly 728 is further configured to help inhibit the patient from snoring, while also assisting the patient in overcoming mild to moderate obstructive sleep apnea and/or other sleep-related issues. It is further appreciated that the Herbst device assembly 728 is also useful for addressing potential TMJ issues.

The design of the Herbst device assembly 728 can be varied to suit the requirements of the oral appliance device 712 and/or to meet the specific anatomical requirements of the patient with whom the oral appliance device 712 is being used. In some embodiments, the Herbst device assembly 728 includes a first Herbst bar 770A, a second Herbst bar 770B that adjustably engages the first Herbst bar 770A, a first Herbst connector assembly 772A that selectively and removably couples the first Herbst bar 770A to the upper appliance member 714 (e.g., toward a front 714F of the upper appliance member 714), and a second Herbst connector assembly 772B that selectively and removably couples the second Herbst bar 770B to the lower appliance member 716 (e.g., toward a rear 716R of the lower appliance member 716). Alternatively, the Herbst device assembly 728 can include more components or fewer components than those specifically noted herein, and/or the Herbst device assembly 728 can have a different design than what is illustrated and described in detail herein.

As provided herein, the first Herbst bar 770A and the second Herbst bar 770B are configured to adjustably engage one another to selectively control the positioning of the lower jaw 17B relative to the upper jaw 17A, such as noted above. More particularly, the Herbst bars 770A, 770B can be set in position relative to one another to allow for a certain degree of movement between the upper appliance member 714 and the lower appliance member 716, and thus between the upper jaw 17A and the lower jaw 17B. For example, in certain embodiments, the Herbst bars 770A, 770B are adjustable relative to one another so as to allow between approximately one millimeter and five millimeters of spacing and/or protrusive titration between the upper appliance member 714 and the lower appliance member 716. When the Herbst bars 770A, 770B are initially set in position relative to one another, the healthcare professional and/or the patient can evaluate whether or not the patient is receiving the desired relief. If the desired relief is not achieved, then the Herbst bars 770A, 770B can be moved relative to one another to another suitable position and again be evaluated.

In the embodiment illustrated in FIG. 7A, the first Herbst bar 770A and the second Herbst bar 770B are configured to engage one other in a telescoping manner. With such design, the Herbst bars 770A, 770B can be easily moved relative to one another, e.g., in one-quarter millimeter increments, to adjust the spacing and/or protrusive titration enabled between the upper appliance member 714 and the lower appliance member 716. Alternatively, the Herbst bars 770A, 770B can be configured to adjustably engage one another in another suitable manner.

The Herbst bars 770A, 770B can be formed from any suitable materials. For example, in one non-exclusive embodiment, the Herbst bars 770A, 770B can be formed from stainless steel. Alternatively, in other embodiments, the Herbst bars 770A, 770B can be formed from other suitable materials.

Additionally, as noted above, the first Herbst connector assembly 772A is configured to removably couple the first Herbst bar 770A to the upper appliance member 714. Similarly, the second Herbst connector assembly 772B is configured to removably couple the second Herbst bar 770B to the lower appliance member 716. The Herbst connector assemblies 772A, 772B can have any suitable design. In many embodiments, the first Herbst connector assembly 772A and the second Herbst connector assembly 772B are substantially similar in design. Alternatively, the first Herbst connector assembly 772A and the second Herbst connector assembly 772B can have a somewhat different design.

In various embodiments, the components of the Herbst connector assemblies 772A, 772B can be formed from any suitable materials and/or can be formed from any suitable manufacturing process. For example, in some non-exclusive embodiments, the components of the Herbst connector assemblies 772A, 772B can be formed from a nylon-based material, e.g., PA 2200 nylon, polyamide 12 nylon, or another suitable nylon material. Alternatively, the components of the Herbst connector assemblies 772A, 772B can be formed from other suitable materials.

Additionally, in certain non-exclusive alternative embodiments, the components of the Herbst connector assemblies 772A, 772B can be manufactured using one of a three-dimensional printer and a selective laser sintering process. Alternatively, the components of the Herbst connector assemblies 772A, 772B can be manufactured using another suitable process.

Figure 7B:
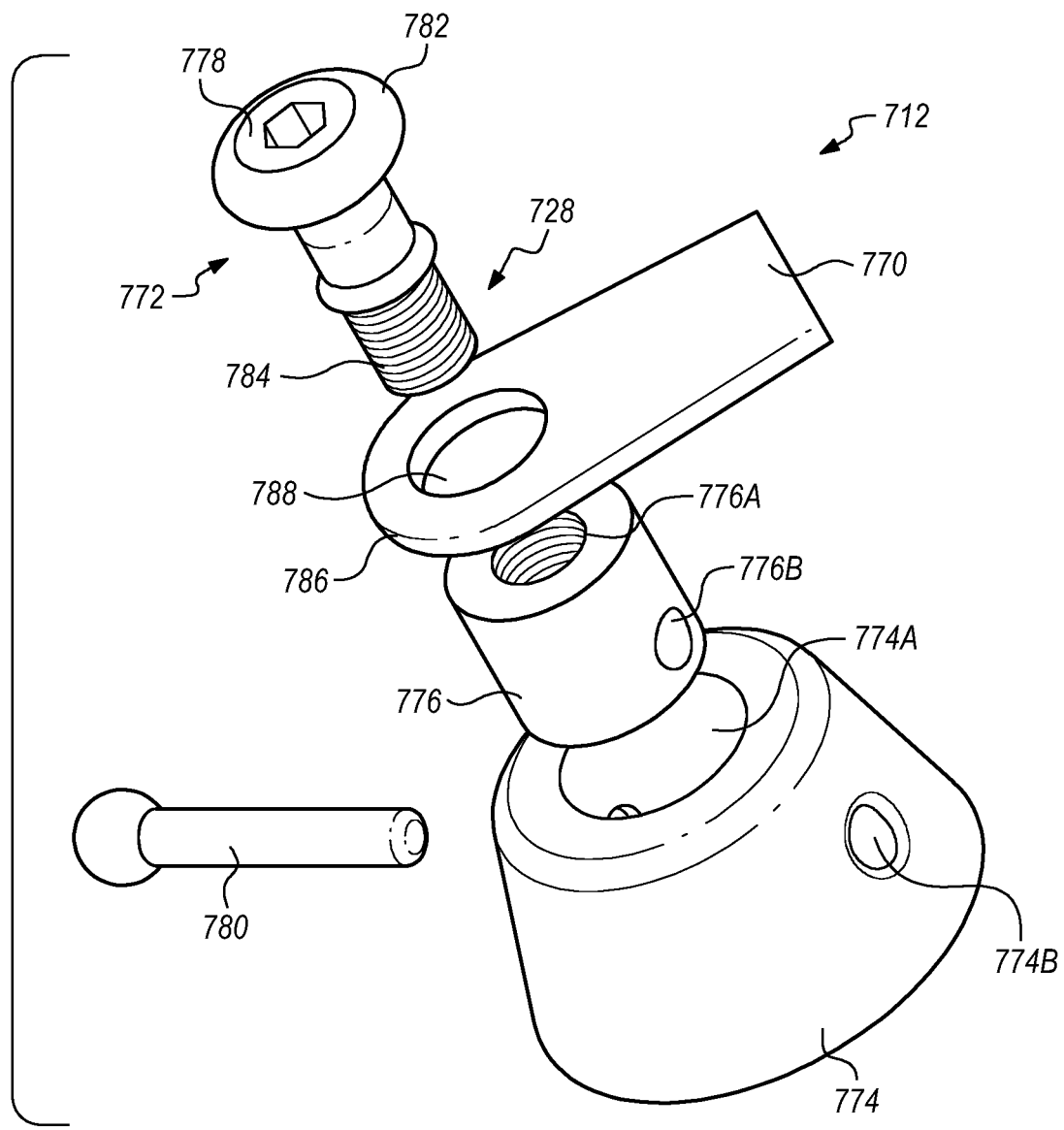
FIG. 7B is an exploded view illustration of a portion of the oral appliance device illustrated in FIG. 7A.

FIG. 7B is an exploded view illustration of a portion of the oral appliance device 712 illustrated in FIG. 7A. In particular, FIG. 7B illustrates an exploded view of an embodiment of the Herbst connector assembly 772, e.g., which can be the first Herbst connector assembly 772A and/or the second Herbst connector assembly 772B, and a portion of one of the Herbst bars 770, e.g., the first Herbst bar 770A or the second Herbst bar 770B, of the Herbst device assembly 728 illustrated in FIG. 7A.

As noted above, the Herbst connector assembly 772 is configured for selectively and removably coupling the first Herbst bar 770A and the second Herbst bar 770B of the Herbst device assembly 728 to the upper appliance member 714 (illustrated in FIG. 7A) and the lower appliance member 716 (illustrated in FIG. 7A) of the oral appliance device 712, respectively. The Herbst connector assembly 772 can have any suitable design. For example, in some embodiments, as shown in FIG. 7B, the Herbst connector assembly 772 can include a coupling base 774, a coupling insert 776, a coupling button 778, and a coupling pin 780. Alternatively, the Herbst connector assembly 772 can have more components or fewer components than what is illustrated and described herein. For example, in one non-exclusive alternative embodiment, the Herbst connector assembly 772 can be designed without the coupling insert 776.

In certain embodiments, the coupling base 774 is secured to and/or is integrally formed with one of the upper appliance member 714 and the lower appliance member 716. As shown, the coupling base 774 is somewhat truncated cone-shaped and includes a first base aperture 774A that extends through a top of the coupling base 774 and that is configured to receive at least a portion of the coupling insert 776 and at least a portion of the coupling button 778. Additionally, the coupling base 774 further includes a pair of second base apertures 774B that extend through opposing sides of the coupling base 774. As described herein below, the second base apertures 774B are configured to receive a portion of the coupling pin 780 when the Herbst bar 770 is being effectively secured or coupled to the appliance member 714, 716.

The coupling insert 776 is configured to be positioned substantially within the coupling base 774 during use of the Herbst connector assembly 772. As shown, the coupling insert 776 is generally annular-shaped and includes a first insert aperture 776A that extends substantially fully through the coupling insert 776 and is configured to receive at least a portion of the coupling button 778. In certain embodiments, as illustrated, the first insert aperture 776A can be internally threaded to threadingly receive and retain a portion of the coupling button 778. Additionally, the coupling insert 776 further includes a pair of second insert apertures 776B that extend through opposing sides of the coupling insert 776. As described herein below, the second insert apertures 776B are configured to receive a portion of the coupling pin 780 when the Herbst bar 770 is being effectively secured or coupled to the appliance member 714, 716.

The coupling button 778 is configured to be positioned at least partially within the coupling insert 776 and/or the coupling base 774 during use of the Herbst coupling assembly 772. The design of the coupling button 778 can be varied. As illustrated, the coupling button 778 includes a button head 782 and a button shaft 784 that extends away from the button head 782. Additionally, as shown, the button shaft 784 can include external threads that are configured to threadingly engage the internal threads of the first insert aperture 776A of the coupling insert 776.

It is appreciated that in embodiments that do not include the coupling insert 776, the coupling base 774 can include internal threads, and the external threads of the button shaft 784 can be configured to threadingly engage the internal threads of the coupling base 774.

Additionally, as shown in FIG. 7B, a bar end 786 of the Herbst bar 770 that is secured or coupled to the appliance member 714, 716 includes a bar aperture 788.

During use of the Herbst device assembly 728, i.e. for purposes of selectively and removably coupling the first Herbst bar 770A to the upper appliance member 714, and selectively and removably coupling the second Herbst bar 770B to the lower appliance member 716, the coupling insert 776 is positioned substantially within the coupling base 774 that is secured to the appliance member 714, 716, such that the second insert apertures 776B are aligned with the second base apertures 774B. Additionally, the coupling pin 780 is positioned to extend through both of the second base apertures 774B and both of the second insert apertures 776B so that the coupling insert 776 can be effectively retained within the coupling base 774. The Herbst bar 770 is then positioned over the coupling insert 776 and/or the coupling base 774 such that the bar aperture 788 is effectively aligned with the first insert aperture 776A and the first base aperture 774A. The button shaft 784 is then extended through the bar aperture 788 of the Herbst bar 770 and threaded into the first insert aperture 776A of the coupling insert 776. Thus, the external threads of the button shaft 784 are positioned to threadingly engage the internal threads of the first insert aperture 776A of the coupling insert 776. At this point, the Herbst bar 770 is effectively, yet removably, secured or coupled to the appliance member 714, 716 via the Herbst connector assembly 772.

It is understood that although a number of different embodiments of an oral appliance device have been illustrated and described herein, one or more features of any one embodiment can be combined with one or more features of one or more of the other embodiments, provided that such combination satisfies the intent of the present invention.

While a number of exemplary aspects and embodiments of the oral appliance device have been shown and disclosed herein above, those of skill in the art will recognize certain modifications, permutations, additions and sub-combinations thereof. It is therefore intended that the present invention shall be interpreted to include all such modifications, permutations, additions and sub-combinations as are within their true spirit and scope, and no limitations are intended to the details of construction or design herein shown.

What is claimed is:

1. An oral appliance device for use within a human mouth having an upper jaw and a lower jaw, the oral appliance device comprising:
   an upper appliance member that selectively engages upper teeth within the human mouth;
   a lower appliance member that selectively engages lower teeth within the human mouth; and
   a Herbst device assembly including (i) a first Herbst bar, (ii) a second Herbst bar that adjustably engages the first Herbst bar to selectively control positioning of the lower jaw relative to the upper jaw, (iii) a first Herbst connector assembly that removably couples the first Herbst bar to the upper appliance member, and (iv) a second Herbst connector assembly that removably couples the second Herbst bar to the lower appliance member, each of the Herbst connector assemblies including (i) a coupling base that is integrally formed with one of the appliance members, the coupling base including a first base aperture and a pair of second base apertures; (ii) a coupling insert that is selectively positioned in the first base aperture, the coupling insert including a first insert aperture and a pair of second insert apertures; (iii) a coupling button including a button shaft that is removably received and retained within the first insert aperture, and (iv) a coupling pin that is positioned to extend through both of the second base apertures and both of the second insert apertures so that the coupling insert is retained in the coupling base.

2. The oral appliance device of claim 1 wherein the first insert aperture has internal threads.

3. The oral appliance device of claim 2 wherein the button shaft includes external threads that are configured to threadingly engage the internal threads of the first insert aperture.

4. The oral appliance device of claim 3 wherein each of the Herbst bars includes a bar end having a bar aperture; and wherein the button shaft is configured to extend through the bar aperture and be threaded into the first insert aperture to removably couple the first Herbst bar to the upper appliance member and to removably couple the second Herbst bar to the lower appliance member.

5. An oral appliance device for use within a human mouth having an upper jaw and a lower jaw, the oral appliance device comprising:
   an upper appliance member that selectively engages upper teeth within the human mouth;
   a lower appliance member that selectively engages lower teeth within the human mouth; and
   a Herbst device assembly including (i) a first Herbst bar, (ii) a second Herbst bar that adjustably engages the first Herbst bar to selectively control positioning of the lower jaw relative to the upper jaw, (iii) a first Herbst connector assembly that removably couples the first Herbst bar to the upper appliance member, and (iv) a second Herbst connector assembly that removably couples the second Herbst bar to the lower appliance member, the Herbst connector assemblies being at least partially formed from a nylon-based material, the Herbst bars being formed from stainless steel;

wherein each of the Herbst connector assemblies includes (i) a coupling base that is integrally formed with one of the appliance members, the coupling base including a first base aperture; (ii) a coupling insert that is selectively positioned substantially within the first base aperture, the coupling insert including a first insert aperture having internal threads; and (iii) a coupling button including a button shaft having external threads that are configured to threadingly engage the internal threads of the first insert aperture so that the button shaft is removably received and retained within the first insert aperture;

wherein the coupling base has a pair of second base apertures; wherein the coupling insert has a pair of second insert apertures; and wherein each Herbst connector assembly further includes a coupling pin that is positioned to extend through both of the second base apertures and both of the second insert apertures so that the coupling insert is retained within the coupling base.

6. The oral appliance device of claim 5 wherein the coupling base, the coupling insert, and the coupling button are each formed from a nylon-based material.

7. The oral appliance device of claim 6 wherein the coupling base, the coupling insert, and the coupling button are each manufactured using one of a three-dimensional printer and a selective laser sintering process.

8. The oral appliance device of claim 5 wherein the first Herbst bar and the second Herbst bar adjustably engage one another in a telescoping manner.

9. The oral appliance device of claim 5 wherein each of the Herbst bars includes a bar end having a bar aperture; and wherein the button shaft is configured to extend through the bar aperture and be threaded into the first insert aperture to removably couple the first Herbst bar to the upper appliance member and the second Herbst bar to the lower appliance member.

10. The oral appliance device of claim 5 wherein the upper appliance member and the lower appliance member are formed from a nylon-based material.

11. The oral appliance device of claim 1 wherein the upper appliance member and the lower appliance member are formed from a nylon-based material.

12. The oral appliance device of claim 1 wherein the first Herbst bar and the second Herbst bar adjustably engage one another in a telescoping manner.

13. The oral appliance device of claim 5 wherein Herbst device assembly is configured to correct an overbite of the human mouth.

14. The oral appliance device of claim 5 wherein Herbst device assembly is configured to position the lower jaw more anteriorly in the human mouth.

15. The oral appliance device of claim 5 wherein Herbst device assembly is configured to inhibit the lower jaw from moving posteriorly.

16. The oral appliance device of claim 1 wherein Herbst device assembly is configured to correct an overbite of the human mouth.

17. The oral appliance device of claim 1 wherein Herbst device assembly is configured to position the lower jaw more anteriorly in the human mouth.

18. The oral appliance device of claim 1 wherein Herbst device assembly is configured to inhibit the lower jaw from moving posteriorly.

19. The oral appliance device of claim 1 wherein the Herbst bars are adjustable relative to one another to allow between approximately one millimeter and five millimeters of spacing between the upper appliance member and the lower appliance member.

20. The oral appliance device of claim 1 wherein the coupling base, the coupling insert, and the coupling button are each manufactured using one of a three-dimensional printer and a selective laser sintering process.

* * * * *